United States Patent [19]
Chung et al.

[11] Patent Number: 5,728,815
[45] Date of Patent: Mar. 17, 1998

[54] BONE AND PROSTATE-DERIVED PROTEIN FACTORS AFFECTING PROSTATE CANCER GROWTH, DIFFERENTIATION, AND METASTASIS

[75] Inventors: Leland W. K. Chung, Houston; James Chan, Sugarland; Christopher Logothetis, Houston; Jer-Tsong Hsieh, Sugarland, all of Tex.

[73] Assignee: Board of Regents, The University of Texas System, Austin, Tex.

[21] Appl. No.: 179,569

[22] Filed: Jan. 7, 1994

Related U.S. Application Data

[63] Continuation-in-part of Ser. No. 859,228, Mar. 30, 1992, abandoned.

[51] Int. Cl.$^6$ .................................................. C07K 14/475
[52] U.S. Cl. ........................ 530/399; 530/350; 530/412; 514/2
[58] Field of Search ................................ 530/350, 399, 530/412; 435/240.1; 514/2

[56] References Cited

PUBLICATIONS

Scopes 1982 Protein Purification — Principles and Practice Springer–Verlag NY Section 4.5.

Hauschka et al. 1986. J. Biol. Chem. 261:12665–12674 Li, et al. 1993. J. Urol. 149 (4 Supple) 481A.

M. Chackal–Roy and B.R. Zetter, *Faseb Journal*, 4(7): A1989, 1990, Abstract No. 1723.

M. Chackal–Roy et al., "Stimulation of Human Prostatic Carcinoma Cell Growth by Factors Present in Human Bone Marrow," *The American Society for Clinical Investigation, Inc.*, 84:43–50, 1989.

Leland, W.K. Chung, "Fibroblasts Are Critical Determinants in Prostatic Cancer Growth and Dissemination," *Cancer and Metastasis Reviews*, 10:263–274, 1991.

Leland, W.K. Chung et al., "Reciprocal Mesenchymal–Epithelial Interaction Affecting Prostate Tumor Growth an Hormonal Responsiveness," *Cancer Surveys*, 11:91–121, 1991.

Martin Gleave et al., "Acceleration of Human Prostate Cancer Growth in Vivo by Factors Produced by Prostate and Bond Fibroblasts," *Cancer Research*, 51:3753–3761, 1991.

Martin Gleave et al., *Journal of Urology*, 145 (4 Suppl.), 213A, 1991, Abstract No. 1.

M.E. Gleave et al., "Prostate and Bone Fibroblasts Induce Human Prostate Cancer Growth in Vivo: Implications for Bidirectional Tumor–Stromal Cell Interaction in Prostate Carcinoma Growth and Metastasis," *Journal of Urology*, 147:1151–1159, 1992.

Martin E. Gleave et al., "Serum Prostate Specific Antigen Levels in Mice Bearing Human Prostate LNCaP Tumors Are Determined by Tumor, Volume and Endocrine and Growth Factors," *Cancer Research*, 52:1598–1605, 1992.

Zetter, Bruce R. et al., "Selective Stimulation of Prostatic Carcinoma Cell Proliferation by Transferrin," *Proceedings of the National Academy of Science*, 89:6197–6201, 1992.

Bruce Alberts et al., "Molecular Biology of The Cell," 2d ed. Ch. 12:682–683.

"Treatment of Metastatic Disease," *Urologic Cancer*, 12:6–7, 1993.

Leland W.K. Chung et al., "Human Prostate Cancer Model: Roles of Growth Factors and Extracellular Matrices," *Journal of Cellular Biochemistry*, Supplement 16H:99–105, 1992.

Jer–Tsong Hsieh et al., "Autocrine Regulation of Prostate–specific Antigen Expression in a Human Prostatic Cancer (LNCaP) Subline[1]," *Cancer Research*, 53:2852–2857, 1993.

Leland, W.K. Chung, "Implications of stromal–epithelial interaction in human prostate cancer growth, progression and differentiation," *Cancer Biology*, 4:183–192,1993.

J.T. Hsieh et al., "Characterization of Non–Androgenic Prostate–Specific Autocrine Factor(s) with Stimulatory Effect on PSA Gene Expression in Androgen–Independent Human Prostate Cancer Cells," *J. of Urol.*, 149:222A, 1993.

J.T. Hsieh et al., "Detection of a Non–Androgen PSA–Inducing Protein Factor(s) in Bone Marrow Aspirates of Patients with Androgen–Refractory Prostate Tumors: A Potential Prognostic Marker(s) for Disease Progression," *J. Urol.*, 149:257A, 1993.

Eamonn Rogers et al., "The Role of PSA in the Treatment of Radiorecurrent Prostatic Adenocarcinoma by Salvage Radical Prostatectomy".

*Primary Examiner*—Vasu S. Jagannathan
*Assistant Examiner*—K. Cochran Carlson
*Attorney, Agent, or Firm*—Arnold, White & Durkee

[57] ABSTRACT

The role for a substantially purified human growth factor preparation is shown to contain a distinct polypeptide with apparent $M_r$ on SDS/PAGE of about 220 kD, and to be distinct from bFGF, with a most active fraction at about 220 kD. A human growth factor polypeptide of 157 kD was identified, in human bone marrow aspirates and from bone stromal cells, by immunoblotting with the mAb MS 329, and by affinity isolation using a MS 329 antibody column. A PSA stimulating autocrine factor, PSAF, that is precipitable in ammonium sulfate at between 60–80% saturation is able to induce PSA expression and secretion, and serves as an indicator of androgen independent prostate cell growth.

15 Claims, 10 Drawing Sheets

BONE AND PROSTATE-DERIVED PROTEIN FACTORS AFFECTING PROSTATE CANCER GROWTH, DIFFERENTIATION, AND METASTASIS

BACKGROUND OF THE INVENTION

The present application is a continuation-in-part of U.S. patent application Ser. No. 07/859,228 filed Mar. 30, 1992, now abandoned, the entire text of which is herein incorporated by reference without disclaimer.

The government may own rights in the present invention pursuant to NCI grant number IR01-CA-56307-01.

1. Field of the Invention

The present invention relates generally to the field of cancer and also to polypeptides with growth-promoting activities. The invention is particularly directed to the identification of growth factors, primarily from bone and prostate tissues, that have the capability to stimulate the growth of prostate cells and which promote the metastasis of prostate cancer to bone tissues. The invention is further directed to novel in vivo and in vitro assay methods, both to detect and quantitate such growth factor activity, and to screen for potential anti-cancer therapeutic substances. The preparation and use of monoclonal antibodies against one such growth factor polypeptide is also disclosed. Also disclosed is a polypeptide that induces the secretion of prostate specific antigen by prostate cells.

2. Description of the Related Art

The increased incidence of prostate cancer during the last decade has established prostate cancer as both the most prevalent cancer, and the second leading cause of cancer deaths, in men (Carter & Coffey, 1990). Most patients dying of prostate cancer experience painful and sometimes crippling osseous metastases with up to 84% having bony metastases at autopsy (Franks, 1956). Prostate cancer is known to selectively spread to the cancellous bones of the axial skeleton, where it is the only malignancy to consistently produce osteoblastic lesions (Cook & Watson, 1968). Frequently, these bony metastatic lesions grow at a more rapid rate than that of primary or other metastatic lesions (Jacobs, 1983).

The treatment strategies available for patients with metastatic prostate cancer have, in the past, focused primarily on androgen deprivation and/or radiation therapy. Such therapeutic modalities have palliative value, but have not resulted in cure or significant increases in patient survival rate. Recently, suramin, a drug known to disrupt the interaction of growth factors and their receptors, was shown to inhibit prostate tumor cell growth both in vitro and in vivo (LaRocca et al., 1990). However, the extreme toxicity of suramin in vivo prevents its clinical use in human treatment.

The "seed and soil" hypothesis initially described in 1989 (Paget, 1989), proposes that tumor cells may selectively grow in certain organs due to their particular properties. More recently, some such properties have been proposed to be relevant to prostate cancer development, including, enhanced adhesion (Nicolson & Winkelhake, 1975; Sherman et al., 1980), chemotaxis (Varani, 1982; Hujanen & Terranova, 1985), or preferential growth at certain sites (Manishen et al., 1985; Hart, 1985).

Several factors have been hypothesized to be responsible for the metastasis of prostate cancer to bone tissues. For example, it has been proposed that prostate cancer cells selectively seed the lumbar spine and pelvis via a paravertebral venous plexus through which retrograde flow from the prostate to the spine may occur at times of increased intraabdominal pressure (Batson, 1940; Shevrin et al., 1988). However, this theory falls short as most tumor cells in the venous circulation also pass through the lungs (Nicolson, 1979) and yet the incidence of clinically apparent lung metastases in patients dying of prostate cancer is low (Elkin & Mueller, 1979; Johnson, 1982). Furthermore, kinetic distribution studies using radiolabeled tumor cells have not shown a correlation between organ seeding and subsequent metastatic formation (Fidler a Nicolson, 1976; Potter et al., 1983), suggesting that factors other than the simple mechanical arrest of tumor cells are responsible for the development of prostate cancer bony metastasis.

Recent work has provided some evidence that prostate cancer cell growth may be under autocrine influences involving androgen-mediated regulation of TGFα, EGF receptor, or bFGF (Wilding et al., 1989; Nonomura et al., 1988; Lu et al., 1989). It has also been suggested that paracrine-mediated pathways involving the stromal compartment play a role in prostate cancer progression (Camps et al., 1990; Chung et al., 1989; Chackel-Roy et al., 1989; Kabalin et al., 1989). Clinically, the interaction between prostate cancer cells and osteoblasts is apparent from the enhanced growth rate of bony metastatic lesions and accompanying osteoblastic reaction. Primary benign and malignant prostatic neoplasms have been shown to express BFGF (Mydlo et al., 1988; Story et al., 1987). Prostatic osteoblastic factor, a soluble substance found in benign hyperplastic and malignant prostatic tissue that stimulates osteoblasts, may well be a FGF-like substance (Jacobs et al., 1979; Nishi et al., 1988), although more recent studies suggest that it may be a distinct and as yet undefined growth factor (Perkel et al., 1990).

Despite many studies, including those described above, it is evident that the factors involved in prostatic carcinogenesis, progression and nonrandom metastasis remain poorly defined. Moreover, the actions of those few growth factors which have been shown to stimulate prostate cell growth in vitro have not been examined in vivo. The identification of growth factors which exhibit prostate cell growth promoting activity in vivo would be an important development, creating new avenues of clinical investigation and treatment.

The current lack of information concerning the in vivo action of such growth factors highlights another drawback which currently exists in the art, that is the lack of an appropriate animal model with which to investigate the many inter-relating factors which may contribute to the progression and metastasis of prostate cancer. This is particularly important as only an in vivo human prostate cancer model is appropriate to asses the complicated mechanisms underlying the metastatic process, which naturally, cannot be assessed solely in vitro.

SUMMARY OF THE INVENTION

Accordingly, the present invention is directed to the identification and purification of novel growth factors, primarily present in bone tissues, but also present in prostate tissues, that have the capability to promote normal prostate cell growth and prostate cancer cell growth and metastases. The invention is further directed to novel in vivo assay methods, both for the identification of factors which promote prostate cancer cell growth, and to the identification of potential therapeutic compounds for use in treatment strategies. The present invention further encompasses the generation of monoclonal antibodies directed against these growth factor polypeptides and their use in cancer diagnosis and treatment.

The growth-promoting factors of the present invention are defined as containing proteins or polypeptides, that have the capability to stimulate prostate cell growth. As used herein, the term "stimulate prostate cell growth" is intended to refer to the capacity of a given composition to promote the growth or proliferation of normal, or cancerous, prostate cells to any detectable degree. Accordingly, the growth factors of the present invention are functionally characterized as having the ability to stimulate the growth of prostate cells, as exemplified by an ability to stimulate the growth of normal prostate cells in culture; or the ability to stimulate the growth of prostate cancer cells such as LNCaP cells.

Further to the functional characterization described above, a growth factor of the present invention is particularly characterized as comprising one, or a combination of, polypeptides being selected from the group consisting of polypeptides characterized as exhibiting an apparent molecular weight on SDS/PAGE, when conducted as described hereinbelow, of about 220 kD. However, it is, of course, generally understood by those of skill in the art that the migration of a polypeptide can vary with different conditions of SDS/PAGE (Capaldi et al., 1977). It will therefore be appreciated that under differing electrophoretic conditions, the molecular weight assignments quoted above may vary.

In important embodiments, the present invention concerns the substantial purification of such prostate cell growth-promoting factor(s) from human bone tissues. The term "substantially purified human growth factor", as used herein, refers to a growth factor composition, isolatable from human bone fibroblasts, from which has been removed various non-growth-promoting components, and which composition substantially retains its prostate cell growth promoting activity. One unit of activity is defined as one soft agar colony stimulated by bone stromal cell-derived protein factors. The specific activity is defined as unit of soft agar colony-forming activity per mg of protein.

Further embodiments of the present invention relate to methods of purifying one or more of the foregoing growth factors. A particularly preferred source for isolating such growth factors is the cell-conditioned media obtained from human bone or prostate fibroblasts. Such conditioned media were chosen by the inventors as a potential sources of prostate cell growth factors because of the frequent metastasis of prostate cancer to the axial skeleton. In that the human bone fibroblast conditioned media was found to be a particularly rich source of growth factors, it is contemplated to be the preferred starting material for the purification of such growth factors. However, other starting materials may also be employed such as, for example, human prostate cancers, human osteogenic sarcomas, or bone marrow aspirates, preferably obtained from prostate cancer patients.

The preferred approach used to isolate such growth factors involves first culturing human bone fibroblasts to produce the prostate growth factor polypeptides. After obtaining the growth factor polypeptides, for example, by removing conditioned media from the cells, the resultant cell-free polypeptides can then be assayed, characterized and used as a starting material for further purification of the growth factors. During the purification process, it is contemplated that assays will be conducted at various intervals using any one of, or a combination of, the assay methods disclosed herein.

A prostate cell growth factor of the present invention has a approximate molecular weight of about 220 kD when determined with a size-exclusion HPLC column. However, it is, of course, generally understood by those of skill in the art that the migration of a polypeptide can vary with different conditions of SDS/PAGE (Capaldi et al., 1977) and with different sizing columns. It will therefore be appreciated that under differing electrophoretic and chromatographic conditions, the molecular weight assignments quoted above may vary.

The method preferred by the present inventors to obtain a substantially purified of about 220 kD human prostate cell growth factor in accordance herewith is affinity chromatography, and in particular, affinity chromatography employing a heparin-Sepharose column. To perform heparin-Sepharose chromatography in this manner one would first pass a sample of the cell-free growth factor polypeptides, for example, as contained within conditioned media, over the column in a low salt containing buffer, such as 10 mM Tris/HCl, 1 mM PMSF, pH 7.4, to allow binding to the column, and then wash the column with the same buffer to remove any non-binding species. The components that bind to the column can be eluted using the above buffer with an increased salt concentration, such as 1M or 2M NaCl, or by employing a buffered salt gradient, for example, of 0–3M NaCl. Following activity assays of the eluted material the active fractions can be identified, and such fractions selected and pooled.

To further characterize this factor, the pooled active fractions can be applied to a size-exclusion HPLC or FPLC column. Fractions found to exhibit growth-stimulating activity may be electrophoresed through both reducing and non-reducing SDS-PAGE gels. The resulting proteins can be electroeluted and tested for growth-stimulating activity.

In an alternative embodiment of the present invention a prostate cell growth factor of the present invention is particularly characterized as comprising a polypeptide characterized as exhibiting an apparent molecular weight of 157 kD as determined by SDS/PAGE in the absence or presence of reducing agents such as β-mercaptoethanol or dithiothreitol when isolated from human bone stromal cells; and an approximate molecular weight of 55 kD as determined by SDS/PAGE in the presence of β-mercaptoethanol when isolated from bone marrow. When p157 is isolated from bone marrow cells the protein migrates at 157 kD only in the absence of reducing agents.

It will be further understood that certain of the polypeptides may be present in quantities below the detection limits of the Coomassie brilliant blue staining procedure usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of each of the polypeptides present within the growth factor. Immunologically-based techniques such as Western blotting using enzymatically-, radiolabel-, or fluorescently-tagged secondary antibodies are considered to be of particular use in this regard.

The growth factors of the present invention are proposed to have utility in a variety of embodiments. Importantly, they are contemplated to be of use in vivo in stimulating the growth of prostate grafts. Also, in that the tumor formed under the stimulation of these growth factors was found to be extremely angiogenic, the growth factors of the present invention are also reasoned to be powerful angiogens, and as such are contemplated to have utility in further clinical embodiments. These include, for example, the promotion of wound healing, organ growth and/or regeneration, and the promotion of epithelial sprouting.

In another embodiment the purified growth factor is a composition comprising a purified human growth factor that is able to stimulate the growth of LNCaP cells in a soft-agar colony forming assay in the presence of antibodies against bFGF, KGF or HGF. In a preferred embodiment the growth factor is isolatable from human bone stromal cell conditioned media and from human bone marrow aspirates. It is further embodied that the approximate molecular weight of the factor as determined by SDS/PAGE under non-reducing conditions be approximately 157 kD, and exhibit a molecular weight of 55 kD in the presence of reducing agents. Another prostate cell growth factor migrates with an approximate molecular weight of about 220 kD when determined by size-exclusion HPLC and is sensitive to heat inactivation and to trypsin digestion.

Furthermore, the growth factors can be used either alone, or in conjunction with each other and other components in tissue culture media. Although preferred, there is no general requirement that the growth factors be provided in their most purified state for use in such embodiments, indeed, it is contemplated that conditioned media containing the growth factors could be directly employed in tissue culture protocols.

Various methods are contemplated to be of use in determining prostate cell growth, i.e., for use in assaying the activity of prostate growth-promoting factors. In preferred embodiments, it is contemplated that such assays may be directed to analyzing the growth of prostate cancer cells, rather than normal prostate cells, simply as a matter of convenience. Such assays include, but are not limited to, in vitro assays such as the uptake and elution of crystal violet dye; the MTT assay for staining and quantitation of live cells in a culture dish; or the incorporation of radioactive, or non-radioactive labels, such as $^3$H-thymidine, or bromodeoxy uridine, respectively, into TCA-precipitable cellular DNA.

A preferred in vitro assay for use in accordance with the present invention is contemplated to be the soft-agar colony-forming assay. The soft-agar colony-forming assay is an indication of transformation, as only transformed cell types can grow in an anchorage-independent manner in soft-agar. Methods of conducting an assay of this kind will be known to those of skill in the art in light of the present disclosure. For example, one could first place plaque agar, such as 0.6% (w/v) agar, into the bottom of each well on a plate or other suitable means of cell culture, and seed the wells with an appropriate number of NbE-1 cells, such as 2,000 cells. A feeder layer of less concentrated agar, such as 0.3 to 0.4% (w/v) agar, containing the potential growth factor substances to be analyzed, would then be placed on top of the cells, from which the candidate substances can diffuse and come into contact with the cells. The number of soft agar colonies subsequently formed would be recorded after an appropriate time interval, for example, on the order of 3 to 4 weeks after seeding. Both the cells and the agar could then be prepared and resuspended in media such as T-medium containing approximately between 5 and 10% fetal calf serum if desired.

In an alternative embodiment the growth factors of the present invention are used for stimulating the growth of pluripotent and totipotent progenitor cells. The growth factors can be used to stimulate the propagation and expansion of stem cells, and in a particularily preferred embodiment human bone marrow stem cells. The methods for isolating, growing, and identifying stem cells are as provided in U.S. Pat. Nos. 4,714,680, 5,061,620, and 5,199,942 incorporated herein by reference. In a particularly preferred embodiment the amount of growth factor for use in growing the stem cells in vitro is between about 50 to 1000 units per $5 \times 10^6$ cells. However, it will be understood by those of skill in the art that the conditions for stem cell growth quoted above may vary.

A particularly important aspect necessary for the present invention is the development of a novel in vivo assay for prostate cancer growth promoting activity. The development of such an assay is based on the inventors' observations that although LNCaP human prostate cancer cells are nontumorigenic when administered at a dose of $<5 \times 10^6$ cells/site, to athymic mice, cancer formation can be induced following co-administration of the non-tumorigenic prostate cells with other cells or compositions. This method therefore allows the inductive capabilities of any cell type, conditioned media, growth factor, hormone, carcinogen, or indeed, any substance one desires, to be examined following the co-administration of the substance and LNCaP cells, or other non-tumorigenic human cells, to mice.

The choice of LNCaP cells for use in such an assay is particularly preferred as such cells have certain advantageous features. For example, LNCaP cells produce prostate specific antigen (PSA), a human tissue-specific tumor marker, which can be used as one method to monitor in vivo prostate cancer cell growth. Moreover, LNCaP cells are the only androgen-responsive human prostate cancer cells that can be consistently grown in vitro. This is an important aspect required for the invention that allows one to conduct parallel in vitro and in vivo assays of various compounds using the same prostate cancer cell types.

To conduct an assay to investigate the capability of a given cell type to elicit LNCaP growth in vivo, one would preferably co-inoculate suitable athymic mice, such as 6–8 week old BALB/c mice, with a number of LNCaP cells and an approximately equivalent number of cells of the cell type to be investigated (herein referred to as the "subject cell type"). Virtually any mode of co-inoculation is considered to be appropriate such as subcutaneous, intravenous, or intraperitoneal injection. The administration of $1 \times 10^5$ to $5 \times 10^6$ cells per inoculant of each cell type is preferred, with the administration of $1 \times 10^6$ LNCaP cells and $1 \times 10^6$ of the subject cells being particularly preferred. One would suspend the cells in an appropriate medium, such as RPMI 1640, phosphate buffered saline of Hank's balanced salts solution with or without 10% fetal bovine serum (FBS), prior to injection.

It is contemplated that one would also generally wish to perform parallel control experiments to confirm the non-tumorigenic nature of the LNCaP and subject cells when administered independently into similar test animals. In such control studies one would administer the same number, or slightly more cells, such as in the order of $2 \times 10^6$ to $5 \times 10^6$ of each cell type resuspended in said inoculant.

Various methods are contemplated to be of use in assessing tumor development. The tumors can be measured at regular intervals and their volumes calculated according to the formula $L \times W \times H \times 0.5236$ (Janek et al., 1975). After sacrifice, the tumors may be excised, weighed, and subjected to various morphological, histological, and biochemical analyses as desired. Furthermore, the choice of LNCaP cells by the inventors also allows the PSA serum levels to be used as an indication of tumor progression.

In further important embodiments, the present invention provides modifications of this in vivo assay model which have been developed to allow the investigation of the effects of substances other than intact cells on prostate cancer growth. This modified method is based upon the adsorption of a substantially purified human growth factor substance onto a solid matrix and the co-administration of the matrix and LNCaP cells to the experimental animal. The adsorbed matrix serves as a reservoir for delivery of the particular substance to the live animal. It is contemplated that this method will be particularly useful for analyzing substances such as conditioned media from various cell types and the partially and fully purified growth factors.

To conduct such an assay one would modify the protocol described immediately above by substituting the co-administration of LNCaP cells with subject cells for the co-administration of LNCaP cells with the adsorbed matrix. A matrix for use in such embodiments is Gelfoam which is commercially available from Upjohn (Kalamazoo, Mich.), although it is believed that any sponge-like matrix, such as, for example, Matrigel, or even agar or agarose, may be employed. One would prepare the matrix under sterile conditions by first pre-soaking it with collagen IV, for example by exposure to 100 µg/ml collagen IV for 12 hours at 4° C., and then exposing it to the test compound(s). The adsorbed matrix would then be minced to allow subcutaneous inoculation, for example using a polytron. A suitable control for an assay such as this would be inoculation with Gelfoam pre-soaked with collagen IV alone.

In that either of the above methods can be utilized to generate an animal bearing a human prostate cancer, the present invention further provides an important model for use in screening for compounds with the potential to inhibit the growth of human prostate cancer. To screen for a substance having the capability to inhibit, retard, or otherwise exert a negative effect on prostate cancer cell growth, one may administer the candidate substance either simultaneously with, or subsequent to, the administration of the cancer promoting agents, i.e., the LNCaP cells and the previously identified stimulatory cells or substances. One would then determine the effect of the candidate inhibitory substance by measuring the degree of tumor formation or regression, or the prevention or inhibition of tumor growth, observed in the presence of the candidate inhibitory substance and comparing it to the tumor status in the absence of the potentially inhibitory substance.

In still further embodiments, the present invention concerns the generation of antibodies, and particularly, monoclonal antibodies (mAbs) against the growth factor polypeptide(s) disclosed herein. Such mAbs will have utility in a variety of applications. These include, for example, the rapid purification of the growth factors by immunoaffinity chromatography, and the clinical use of mAbs or mAb-conjugates in diagnostic, prognostic, imaging, and therapeutic strategies for the treatment of prostate cancer in man. In a preferred embodiment the monoclonal antibody reacts with a protein of 157 kD.

The in vivo human prostate cancer model disclosed herein is contemplated to be particularly useful in testing mAbs to identify those that are suitable for clinical use. For example, one may test the ability of mAbs or mAb-conjugates to inhibit prostate cancer growth or metastasis in the mouse model, prior to clinical trials in human subjects. It will be understood, however, that mAbs which are not considered to meet the criteria for clinical use may nonetheless have utility in other embodiments, such as in growth factor purification by affinity column chromatography or in Western blotting, ELISA, or other immunological screening assays.

It is proposed that such anti-growth factor mAb generation may be achieved most readily through the use of a modified immunization protocol. It is contemplated that the initial immunization of an experimental animal, such a mouse, would be performed according to the standard practice in the art. However, for the booster inoculation, the use of the following method is proposed to be advantageous in that it will allow the optimal exposure of splenocytes to the booster antigen. The immunized mice should be surgically opened to expose the spleen and a sterile solution of the growth factor antigens be injected directly into the spleen. The mouse would then be sutured and allowed to recover.

Blood samples of the immunized mice may be analyzed for the presence of circulating antibodies to the growth factors, and those mice producing reasonable titers of circulating antibodies would be sacrificed and their spleens will be removed for cell fusion. A mouse myeloma cell line proposed to be of use for hybridization is the 8-azaguanine-resistant mouse myeloma SP2/0 non-producer cell line, which is known to be HAT sensitive. Cells may be fused according to any of the methods known in the art, such as, by using polyethylene glycol (PEG), and later screened for antibody production, for example, by employing an ELISA or immunoblot technique.

As mentioned above, the LNCaP cell tumor model has the advantages of growing LNCaP cells both in vivo and in vitro, and observing the production of PSA by the LNCaP cells. Using the inductive model described by Chung et al., (1989) and Chung (1993), tumorigenic and androgen-independent LNCaP sublines were derived. One such line, C4, was found to produce a proteinaceous substance(s) that was capable of stimulating PSA production via a pathway independent of the androgen receptor (Hsieh et al., 1993). Also disclosed is a factor that induces expression of prostate specific antigen (PSA) and its secretion into medium or serum. The PSA stimulating autocrine factor, or PSAF, was found also to be present in the blood and bone marrow aspirates of patients with prostate cancer, and is precipitable by ammonium sulfate fractionation at a level between 60–80% saturation. Further, the inventors have clinical evidence that the levels of PSAF may be inversely correlated with the prognosis of patients with metastatic prostate cancer. PSAF activity as assayed by the induction of PSA expression by LNCaP cells serves as an index of androgen-independence or androgen refractory growth of the prostate cells.

As used herein, the phrase "induce the expression of prostate specific antigen (PSA) in serum" is intended to refer to the capacity of a given composition to increase the concentration of serum or supernatant PSA. PSA is produced exclusively by prostate epithelium and is used extensively as a serum marker for the diagnosis and prognosis of prostate cancer.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
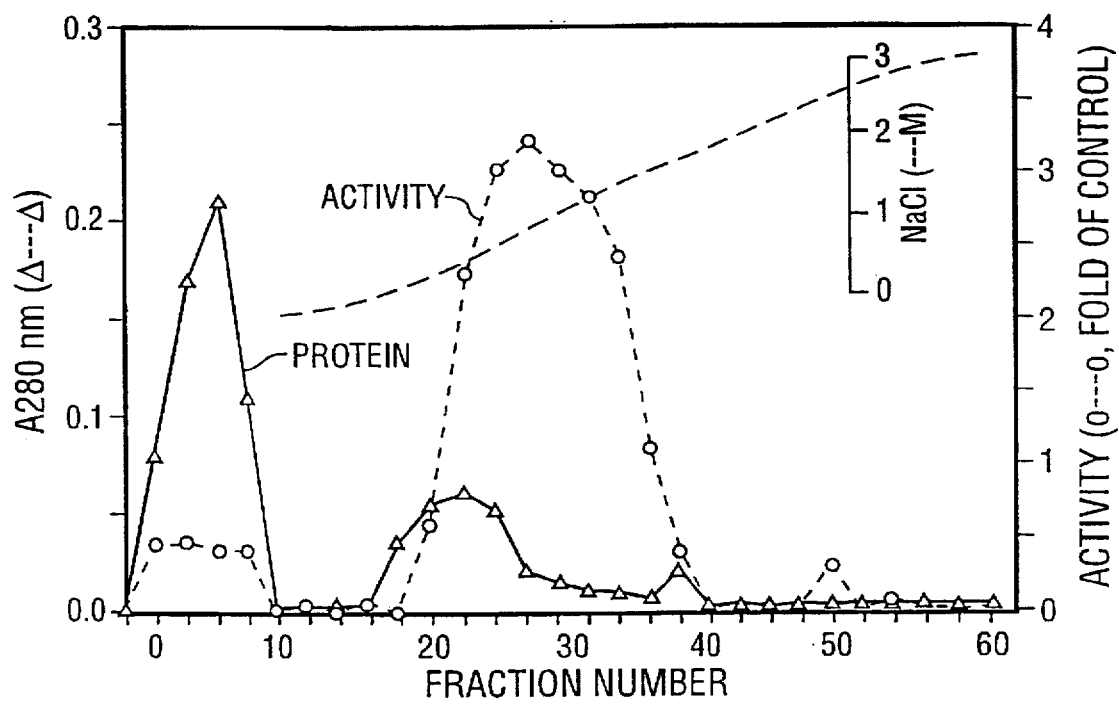
FIG. 1. Heparin-sepharose affinity chromatographic elution of conditioned media isolated from human bone marrow stromal cells. A fraction eluted by 1.0M NaCl exhibited the greatest growth-stimulating activity.

Cellular interactions between mesenchymal and epithelial cells are believed to be an integral part of embryonic development (Kratochwil, 1972) which continues through adulthood by maintaining differentiated organ growth and function (Frank et al., 1970). These interactions have also been proposed to be involved in the regulation of hormonal responsiveness (Cunha & Chung, 1981) and may play an important inductive and/or permissive role in the pathogenesis of tumor growth (Pitot et al., 1985; DeCosse et al., 1973; Hodges et al., 1977) and metastases (Chackel-Roy et al., 1989; Horak et al., 1985). The growth of a number of epithelial malignancies are influenced by their surrounding stroma, including the urinary bladder (Camps et al., 1990; Hodges et al., 1977), prostate (Camps et al., 1990; Kabalin et al., 1989), colon (Picard et al., 1986), and breast (Miller et al., 1989).

The present disclosure presents the results from studies directed to identification and characterization of growth factors which promote prostate cell growth. Also examined is the question of whether fibroblast-specificity exists in affecting the growth of human prostate cancer, and in particular, of the lymph node derived prostate cancer cell line (LNCaP).

LNCaP cells were chosen for several reasons. LNCaP cells have previously been shown to be nontumorigenic when injected subcutaneously in athymic mice with less than $4 \times 10^6$ cells/inoculum (Horoszewicz et al., 1983). This observation was confirmed by the present inventors, and further extended by their discovery that LNCaP cells are nontumorigenic even at higher doses. Thus the inductive capabilities of specific growth factors can be examined following their co-administration to mice along with LNCaP. Secondly, the LNCaP cell line is the only prostate cell line that secretes prostate specific antigen (PSA) (Papsidero et al., 1981), a human tissue-specific tumor marker used clinically to monitor in vivo prostate cancer cell growth (Stamey et al, 1987; Ford et al., 1985). Thirdly, LNCaP cells are androgen-responsive both in vivo (Sonnenschein et al., 1989) and in vitro (Schuurmans et al., 1989) which provides scope for the sex-dependent differences in chimeric tumor growth to be assessed.

Furthermore, and importantly, of the androgen-responsive human prostate cancer models available, including PC82, HONDA, and LNCaP cell lines, only the LNCaP can be consistently grown in vitro (Isaacs, 1987). The inventors have exploited these properties and have developed a parallel in vitro and in vivo cell-cell interaction assays, that allows, for the first time, the results from dual model systems using the same cell types and factors to be assessed. Moreover, results from such coordinated in vitro and in vivo studies can be more confidently applied to the clinical situation.

The in vivo assay system enabled herein is based upon the co-administration of LNCaP cells to athymic mice along with a growth factor composition. The effect of the composition being analyzed can then be assessed by determining the degree of tumor growth in the co-inoculated animals and compared to the control growth observed (if any) in animals given either LNCaP cells, or the test composition, alone.

To analyze the compositions the inventors have developed a modified version of the assay based upon the adsorption of concentrated substance(s) onto a solid matrix and the co-administration of the matrix and LNCaP cells to an experimental animal where the adsorbed matrix acts as a reservoir for the in vivo delivery of the test substance(s).

The results disclosed herein demonstrate that certain fibroblasts can induce LNCaP tumor growth in vivo in a cell-type specific and androgen-dependent manner. Of the 6 fibroblast cell lines analyzed, bone fibroblasts, followed by the prostate-derived fibroblasts, were found to be the most effective in stimulating LNCaP cell growth both in vivo and in vitro. The presence of bidirectional paracrine pathways between LNCaP and fibroblast cells is illustrated in vivo by the development of sarcomas with the co-inoculation of LNCaP cells and nontumorigenic rUGM and 3T3 fibroblasts. Similar effects are also apparent in vitro as LNCaP and rUGM conditioned media produce bidirectional increases in growth in a paracrine-, but not autocrine-, mediated fashion. These observations suggest that LNCaP and fibroblast cells secrete factors that produce a more favorable microenvironment for tumorigenesis by reciprocally promoting growth, adherence or angiogenesis.

LNCaP cells participated in chimeric tumor formation preferentially in males, demonstrating initial in vivo androgen-sensitive growth. These results, along with their in vitro androgen sensitivity, further support the view that the initial growth of LNCaP cells in vivo may be androgen-responsive (Sonnenschein et al., 1989).

Using this novel method, the LNCaP androgen-refractory cell lines, $C_4$ and $C_5$ have been shown, for the first time, to be tumorigenic and to secrete high levels of PSA autonomously, i.e., in the absence of androgen. Both of these characteristics are typically found in human prostate cancer as it undergoes transformation to enter the hormonally refractory state. The identification of factors produced by such refractory cells may impact on the development of new therapeutic approaches to address the problem of hormonally refractory prostate cancer cell growth.

Results from studies using a solid matrix adsorbed with conditioned media indicated that non-dialyzable factor(s) from bone fibroblast conditioned media samples alone could indeed induce LNCaP growth in vivo. This is the first demonstration that LNCaP tumor growth in vivo can be initiated by specific soluble growth factors derived from bone fibroblast cells. These results underscore the importance of growth factors in prostate cancer growth and progression.

The conditioned media derived from the $C_4$ and $C_5$ cell lines adsorbed to a solid matrix supported the growth of the LNCaP parent cell line. This was the first demonstration the LNCaP tumor growth in vivo can be initiated by specific soluble growth factors. These results underscore the importance of growth factors in prostate cancer cell growth.

In further purifying the growth factors, by employing heparin-sepharose chromatography, it was determined that the substantially purified fraction contained a novel polypeptide with apparent molecular weights on SDS/PAGE of about 220 kD. This polypeptide was found to be distinct from bFGF by a number of criteria including differential elution from heparin sepharose columns and distinct immunoreactivity.

The presence of a novel 157 kD growth factor polypeptide within the active fractions was not initially detected, presumably as it was masked by an irrelevant and inactive polypeptide also present in the control media, or the presence of an inactivating subunit. Its presence was shown following the generation of an anti-growth factor mAb, MS 329, which reacts with a 157 kD protein that is present only in the active fractions, such as $P_1$ and P2 (see FIG. 3, and Example 2), but absent from the control media.

Skeletal tissues are known to produce various growth factors (Canalis et al., 1988; Wergedal et al., 1986; Sampath et al., 1986; Globus et al., 1989; Hauschka et al., 1986) including bFGF (Globus et al., 1989). Osteoblasts are the principal source of synthesis and deposition of bone matrix and the site where bFGF is stored and mediates its mitogenic activity (Globus et al., 1989; Hauschka et al., 1986). bFGF promotes LNCaP cell growth, and may also act in a paracrine fashion to stimulate metastatic cancer cell growth (Lu et al., 1989; Ensoli et al., 1989), but bFGF itself does not appear to be an active component of the growth factors disclosed herein. However, as anti-bFGF antibodies inhibited the bone fibroblast growth factor stimulatory action on prostate epithelial cells, albeit only modestly, the possibility remains that a bFGF-like protein may be responsible, in part, for the growth factor activity which stimulates prostate cell growth in vivo and in vitro.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

IDENTIFICATION OF FACTORS PRODUCED BY PROSTATE AND BONE FIBROBLASTS THAT ACCELERATE HUMAN PROSTATE CANCER CELL GROWTH IN VITRO

Materials and Methods

1. Cell Lines and Cell Culture

LNCaP cells, passage 29, were obtained from Dr. Gary Miller (University of Colorado, Denver, Colo.) and grown in RPMI 1640 (Irvine Scientific, Santa Anna, Calif.) with 10% fetal bovine serum (FBS). Phenotypically, the cells resembled parental lines as evidenced by the results of karyotypic analysis and androgen receptor analysis. The LNCaP sublines (C4 and C5) were established from a parental LNCaP tumor grown in a castrated host, and demonstrated androgen independent cell growth. The LNCaP (M) subline was derived in a non-castrated host.

The six nontumorigenic mesenchymal cell lines analyzed in this study are as follows: a fetal urogenital sinus mesenchyme-derived cell line (rUGM) from 18-day old Noble rat fetuses, developed as described by Chung et al., 1984. rUGM cells were maintained in DMEM (Gibco Laboratories, Grand Island, N.Y.), 5% calf serum (CS), and passages 14–16 were used. A human bone fibroblast cell line, MS, derived from an osteogenic sarcoma, was established by Dr. A. Y. Wang (The University of Texas M.D. Anderson Cancer Center, Houston, Tex.). MS cells were maintained in T-medium (80% DMEM, 20% F12K [Irvine Scientific], 3 g/l NaHCO$_3$, 100 u/ml penicillin G, 100 µg/ml streptomycin, 5 µg/ml insulin, 13.6 pg/ml triiodothyronine, 5 µg/ml transferrin, 0.25 µg/ml biotin, and 25 µg/ml adenine) with 5% FBS; passages 29–33 were used. A rat prostatic fibroblast line, NbE-1, was established from normal Noble rat ventral prostate gland as described previously (Chang & Chung, 1989). NbE-1 cells were maintained in DMEM and 5% CS and nontumorigenic passages 18–22 were used. Normal adult human lung fibroblasts, CCD16 (American Tissue Culture Catalogue CCL 204), were supplied by Dr. J. Roth (Dept. of Thoracic Surgery, UT M.D. Anderson Cancer Center, Houston, Tex.), and passages 14–16 were used. NIH-3T3 cells (ATCC #6587), derived from embryonic mouse tissue, were supplied by Dr. D. Becker (UT M.D. Anderson Cancer Center, Houston, Tex.) and maintained in DMEM with 5% CS. Normal rat kidney (NRK) fibroblasts (ATCC #6509) were grown in DMEM with 5% CS and passages 10–12 were used.

Conditioned media from LNCaP and all 6 fibroblast cell lines was collected and prepared as follows: Cells were cultured in 150 mm tissue culture dishes (Falcon, Becton Dickinson Laboratories, Lincoln Park, N.J.) with T-medium, 2% TCM, a serum-free defined media supplement (Celox Co., Minnetonka, Minn.), and 2% FBS until 60–70% confluent, washed with PBS/EDTA and changed to serum-free T-medium containing 2% TCM only. After 48 hours, the conditioned media was removed, filtered through a 0.2 µm filter (Nalge Co., Rochester, N.Y.), and 0.1 mM phenylmethyl-sulfonylfloride (PMSF, Sigma) was added. Protein concentrations in the conditioned media were determined using a protein assay (Bio-Rad Laboratories, Richmond, Calif.), and ranged from 70–100% of control (T-medium and 2% TCM; 1.3 mg/ml). The conditioned media was dialyzed at 4° C. against distilled water containing 0.1 mM PMSF using Spectra/Pot 3 dialysis membranes (M,>3500 dalton, PGC Scientifics, Gaithersburg, Md.) for 96 hours, changing the water after 48 hours. The samples were lyophilized to dryness and reconstituted in T-medium to ten times concentration (10×), filtered, and diluted to the desired working concentration (0.1 to 2×) with T-medium containing 2% TCM.

2. Assessment of in vivo Tumor Growth

To determine the ability of specific fibroblasts to elicit LNCaP growth in vivo, 6–8 wk old athymic nude mice (BALB/c strain, Charles River Laboratory, Wilmington, Mass.) of both sexes were co-inoculated subcutaneously with $1 \times 10^6$ LNCaP cells and $1 \times 10^6$ of one of the 6 fibroblast cell lines described above. Up to $5 \times 10^6$ LNCaP cells and $2 \times 10^6$ of each of the fibroblast cell lines were injected alone as controls to assess their tumorigenicity. The cells were suspended in 0.1 ml of RPMI 1640 with 10% FBS prior to injection and inoculated via a 27 gauge needle. Tumors were measured twice weekly and their volumes were calculated by the formula L×W×H×0.5236 (Janek et al., 1975). At the time of sacrifice, sternotomy was performed and a cardiac puncture was carried out to obtain serum for PSA analysis.

Tumors were excised, weighed, and subjected to various morphological and biochemical analyses. Similarly, in vivo tumor cell growth was also measured using NbE-1 or 3T3 cells.

Further studies were performed to determine whether LNCaP tumor growth in vivo could be affected by soluble growth factors alone. LNCaP cells were injected along with a Gelfoam preparation (Upjohn, Kalamazoo, Mich.), adsorbed with type IV collagen (Collaborative Research, Bedford, Mass.), endothelial cell derived growth factor (ECGF) (Collaborative Research), and ten times concentrated rUGM or MS conditioned media. This novel matrix system was developed through modification of a previously described procedure (Thompson et al., 1988) and serves as a reservoir for delivery of biologically active factors in vivo. EGF was chosen as a marker of physiologic response to determine whether it could retain its biologic activity during this procedure, and whether angiogenesis alone would be sufficient to promote tumor formation. rUGM and MS conditioned media were used because these cells could induce LNCaP growth in vivo. Basic fibroblast growth factor (bFGF, Collaborative Research) was also used because of its mitogenic effect on LNCaP cells in vitro.

Under sterile conditions, Gelfoam, a solid gelatin sponge, was pre-soaked with 100 µg/ml collagen IV for 12 hours at 4° C., followed by either 1 µg/ml EGF, bFGF, or ten times concentrated stromal conditioned media for 1 hour. The Gelfoam was then minced using a polytron homogenizer to allow subcutaneous inoculation via an 18 gauge needle. Following subcutaneous injection of 0.1 ml Gelfoam, the same site was injected with $2 \times 10^6$ LNCaP cells using a 27 gauge needle. For controls, $2 \times 10^6$ LNCaP cells were inoculated with Gelfoam and collagen IV, with or without EGF. Tumor incidence and size was monitored as described above.

3. Histology and Immunohistochemistry

For routine histology, specimens were fixed in 10% neutral buffered formalin and embedded in paraffin. Eight micron fixed sections were cut and stained with hematoxylin and eosin (H&E). For immunohistochemical studies, specimens were deparaffinized with xylene, rehydrated with 70% ethanol, and treated with 0.1% trypsin for 10 min at 37° C. Sections were then incubated with monoclonal antibodies prepared against cytokeratin, PSA, or prostatic acid phosphatase (PAP) (Biogenex, Dublin, Calif.). An avidin-biotin complex method was used with all specimens using fast red TR or AEC as chromogens (Biogenex). Slides were counterstained with aqueous hematoxylin and mounted with glycerol for visual inspection and photography.

4. Determination of Serum PSA Values

Animals were killed by cardiac puncture under methoxyfluorane anesthesia. Blood was allowed to clot at 37° C. and centrifuged, and the serum was stored at −20° C. PSA values were determined using a dual reactive enzymatic immunoassay kit (TandemTM-E PSA) with a lower limit of sensitivity of 0.4 ng/ml (Hybritech Inc., San Diego, Calif.).

5. DNA Isolation and Southern Blot Analysis and RNA Isolation and Northern Blot Analysis Tissue DNA was isolated from tumors as described by Davis (1986). DNA concentration was determined with a spectrophotometer. DNA specimens were applied to Zetaprobe membranes (Bio-Rad) then baked at 80° C. for 90 minutes prior to hybridization with a $^{32}$P-labeled human Alu repetitive sequences probe (Oncor, Gaithersburg, Md.).

Total cellular RNA was prepared from frozen tissues by the 4M guanidinium thiocyanate extraction method (Chomcjymski & Sacchi, 1987). Typical yields of total cellular RNA were about 300 μg/200 mg tissue as quantified spectrophotometrically using 40 μg RNA/$A_{260}$ unit. RNA was denatured in 50% formamide/18% formaldehyde at 55° C. and fractionated by electrophoresis in a 0.9% denaturing formaldehyde agarose gel. Samples were transferred onto a Zetaprobe membrane (Bio-Rad) by capillary method, and the membrane was then baked for 2 hours at 80° C. The membrane was then prehybridized in the presence of 1M NaCl, 10% dextran sulfate, 1% SDS, and 200 μg/ml salmon sperm DNA for at least 2 hours at 65° C. Hybridization was carried out at 65° C. overnight with a random-primer-labeled probe as indicated. The PSA cDNA, and sequence specific hGK-1 and PSA oligonucleotide probes were obtained from Dr. D. Tindall (Mayo Clinic, Rochester, Minn.) (Lundwall & Lilja, 1987). Finally, the membrane was washed under high stringency conditions (0.5×SSC, 1% SDS at 65° C.). Autoradiograms were prepared by exposing Kodak X-Omat AR film to the membrane at −80° C. with intensifying screens.

6. Mitogenic Assays

To determine the mitogenic activity of androgens (testosterone and dihydrotestosterone, Sigma) and conditioned media prepared from various types of fibroblasts on the growth of human LNCaP cells in vitro, a 96-well assay was used based on the uptake and elution of crystal violet dye by the cells in each well (Gillies et al., 1987; Kanamarus & Yoshida, 1989). Various defined growth factors, including basic fibroblast growth factor (bFGF), transforming growth factors alpha and beta (TGFα, TGFβ) and epidermal growth factor (EGF) (Collaborative Research) were also tested.

Using 96 well plates, 3,000 LNCaP, 500 MS, or 200 rUGM cells were plated per well (Falcon) in T-medium containing 1% charcoal stripped CS and 2% TCM. Twenty-four hours later, the cells were placed in serum-free condition (see above) with various concentrations of androgens, growth factors, or conditioned media. To avoid stripping poorly adherent LNCaP cells with each media change, media was partially removed by gentle suction and 100 μl of fresh media was added in 50 μl aliquots. The medium was changed every 2 days; 7–10 days later the cells were fixed in 1% glutaraldehyde (Sigma), and stained with 0.5% crystal violet (Sigma). Plates were washed, air-dried, and the dye was eluted with 100 μl Sorensen's solution (9 mg trisodium citrate in 305 ml distilled $H_2O$, 195 ml of 0.1N HCl, and 500 ml 90% ethanol). The absorbance of each well was measured by a Titertek Multiskan TCC/340 (Flow Laboratories, McLean, Va.) at 560 nm. Control experiments demonstrated that absorbance is directly proportional to the number of cells in each well.

7. Androgen Receptor Assays

Whole cell androgen receptor assays were performed as described previously by Guthrie et al. (Guthrie et al., 1990), with the following modifications. LNCaP cells were plated in T-medium plus 5% FBS in 6 well plates (Falcon) and downshifted to 0.4% charcoal-stripped calf serum 24 hours preceding the assay. Just prior to beginning the assay, this medium was removed and cells were washed twice with PBS/EDTA, and T-medium with various dilutions of $^3$H-R1881 (methyltrienolone 81.8 Ci/mmol, DuPont Co., Wilmington, Del.) was added to appropriate wells. In some wells, unlabeled R1881 (200-fold of [$^3$H-R1881]) was added to determine the extent of nonspecific binding. Following a 90 minute incubation at 37° C., the media was removed, cells were washed with ice cold PBS/EDTA, and 1 ml of 100% ethanol was added to each well. A 500 μl aliquot was added to a scintillation vial and counted with a scintillation counter (Beckman Instruments, Inc., Houston, Tex.).

Results

1. Effect of Co-inoculated Fibroblasts on LNCaP Tumor Growth

The incidence of tumor formation in mice co-inoculated with LNCaP cells and various types of fibroblasts was compared (Table 1). The observation period for all injections was 3 months. LNCaP and all fibroblast cell lines were found to be nontumorigenic (0/20) with injections of up to $5 \times 10^6$ or $2 \times 10^6$ cells, respectively. No significant sex differences in tumor formation were observed in hosts coinoculated with LNCaP and rUGM cells, with an overall tumor incidence of 61% for males and 50% for females. The average latency period for measurable tumor growth was 42 days in male and 45 days in female hosts. No difference in tumor volume or latency period was observed by increasing the rUGM inoculum from $1 \times 10^5$ to $1 \times 10^5$ cells. Mean tumor volume was 322±106 mm$^3$. No sex differences in the incidence of tumor formation was observed in hosts coinoculated with LNCaP and 3T3 cells (67%, mean tumor volume 420 mm$^3$). In contrast, marked sex differences in tumor induction were observed with coinoculation of LNCaP and human bone (MS) or LNCaP and rat prostatic (NbE-1) fibroblasts, as these tumors formed only in male hosts (62% and 17%, respectively). Mean tumor volume for LNCaP/MS and LNCaP/NbE-1 tumors was 238±74 mm$^3$ and 72±52 mm$^3$, respectively. Lung CCD16 and NRK fibroblasts did not induce chimeric tumor growth in either sex. The histomorphology and relative content of LNCaP cells in the various fibroblast-induced tumors differed markedly, as characterized below.

TABLE 1

| Fibroblast | Host | Incidence of tumor formation | Histomorphology of tumors | |
|---|---|---|---|---|
| | | | Carcinosarcoma | Sarcoma |
| MS | Male | 8/13 (62%) | 8/13* (62%) | 0/13 (0%) |
| | Female | 0/10 (0%) | | |
| rUGM | Male | 31/51 (61%) | 16/51 (31%) | 15/51 (30%) |
| | Female | 18/36 (50%) | 2/36 (6%) | 16/36 (44%) |
| NbE-1 | Male | 3/18 (17%) | 3/18 (17%) | 0/18 (0%) |
| | Female | 0/10 (0%) | | |
| CCD16 | Male | 0/20 (0%) | | |
| | Female | 0/6 (0%) | | |
| NRK | Male | 0/20 (0%) | | |
| | Female | 0/10 (0%) | | |

*All carcinomas with no sarcomatous component

In further studies of this kind, only nonirradiated human bone stromal (MS) cells were found to be active in promoting LNCaP tumor formation (Table 2).

TABLE 2

| Fibroblast | LNCaP Cell | Incidence of tumor formation* |
|---|---|---|
| None | $2 \times 10^6$ | 0/6 (0%) |
| MS $1 \times 10^6$ (nonirradiated) | $1 \times 10^6$ | 15/17 (88%) |
| MS $1 \times 10^6$** (irradiated) | $1 \times 10^6$ | 0/8 (0%) |
| CCD16 $1 \times 10^6$ | $1 \times 10^6$ | 0/6 (0%) |

*Incidence of tumor formation was recorded 32–54 days after inoculation
**The cells were irradiated with 40 Gy before coinoculation with LNCaP Cells 2. Characterization of the Chimeric Tumors Chimeric tumors were characterized histomorphologically, immunohistochemically, and biochemically. A difference in histomorphology of LNCaP/rUGM chimeric tumors was noted between males and females: in males, 51% of tumors (or 31% of inoculation sites) were carcinosarcomas, with a predominantly epithelioid component separated by strips of mesenchymal cells, while 89% (16/18) of the tumors in females were pure sarcomas. MS bone fibroblasts were found to be the most potent inducer of LNCaP tumor formation. All tumors were carcinomas composed of sheets of poorly differentiated epithelial cells with minimal mesenchymal cells and formed at 62% of inoculated sites in male hosts; no tumors formed in female hosts. NbE-1 cells were also capable of inducing LNCaP tumor growth in male hosts, but not as well as the MS or rUGM cells; three carcinomas formed from 18 inoculations (17%). LNCaP/3T3 tumors, however, were all sarcomas with no epithelial component. No tumors formed with coinoculation of LNCaP with human lung CCD16 or NRK fibroblasts.

The prostatic origin of the epithelial cells participating in the MS-, rUGM-, and NbE-induced tumor formation in male hosts was confirmed with immunohistochemical staining procedures using monoclonal antibodies directed against PSA, PAP, and cytokeratin. The epithelial component of these tumors stained intensely positive for PSA using fast red TR as the chromogen; with no staining of the associated stromal component. The epithelial component of these tumors also stained positive for PAP and cytokeratin, but in an irregular and scattered manner compared to PSA. In contrast, sarcomas arising from LNCaP/rUGM inoculations in females and LNCaP/3T3 inoculations in both males and females stained negatively for PSA, PAP, and cytokeratin.

Biochemical characterization using Northern and Southern hybridization techniques corroborated the histologic findings to confirm the human prostatic origin of the epithelial component of the chimeric tumors. The LNCaP/rUGM tumors in male hosts contained a predominantly human component as manifested by the presence of Alu-sequences in 6 (2 weakly) of 7 tumors examined, compared to none in female tumors. PSA expression was more variable in these tumors and did not correlate consistently with the histomorphologic and Southern dot-blot analysis, likely because of different sampling from a heterogenous carcinosarcoma. All LNCaP/MS tumors were strongly positive for PSA expression and human-specific Alu sequences on Northern and Southern analysis, respectively. None of the LNCaP/3T3 tumors that formed had any human prostate component.

3. Serum PSA Levels

Sera from male and female mice bearing chimeric tumors were assayed for PSA using the Hybritech enzyme immunoassay. Four control males injected with human bladder transitional cell carcinoma cells (Stamey et al, 1987) had undetectable PSA levels, as anticipated, as PSA is a human prostate marker. Significant differences in median serum PSA values were observed among the different fibroblast-induced tumors as well as male and female hosts, paralleling differences in their histomorphology. LNCaP/MS tumors were associated with consistently elevated serum PSA levels ranging from 25.1 ng/ml to 323 ng/ml, with a median of 68.1 ng/ml (n=6). Similarly, male hosts bearing LNCaP/NbE-1 tumors had elevated serum PSA (n=4). However, nontumor-bearing females with LNCaP/MS and LNCaP/NbE-1 injections had undetectable serum PSA levels. Serum PSA values in males with LNCaP/rUGM tumors ranged from 0.4 to 348 ng/ml with a median of 16.1 ng/ml; 11 of 12 males had detectable levels and 3 had levels 100 ng/ml. In all but one of the 8 females with LNCaP/rUGM tumors, serum PSA was undetectable. All animals with LNCaP/3T3 tumors, as well as those inoculated with LNCaP/CCD16 or LNCaP/NRK cells, had undetectable serum PSA levels.

4. LNCaP Androgen Sensitivity and Androgen Receptor Content

To determine whether the LNCaP cell line was indeed androgen-sensitive, the in vitro mitogenic effects of testosterone and DHT in serum-free and chemically-defined medium were evaluated. Peak responses were seen with $5 \times 10^{-10}$M testosterone and $1 \times 10^{-10}$M DHT, producing 62% and 43% increases, respectively, in cell number over 9 days when compared to controls grown in serum- and hormone-free media. Whole cell androgen receptor assays revealed the presence of a substantial number of high affinity androgen receptors ($K_d$=0.23 nM; $B_{max}$=332 fmol/mg protein.

5. Effect of Defined Growth Factors on LNCaP Cells in vitro

To identify possible mitogens involved in LNCaP cell growth, the dose-response relationship between LNCaP cells and bFGF, EGF, TGFα, and TGFβ was investigated. Using concentrations ranging from 0.1 to 50 ng/ml, bFGF stimulated LNCaP cell growth 180% in a concentration-dependent manner compared to cells grown in serum-free media alone. Minimal increases in cell number compared to controls were seen with EGF and TGFα over a wide range of concentrations. TGFβ, at 1 ng/ml, inhibited LNCaP cell growth by 70%. Time course studies also revealed that bFGF (50 ng/ml) stimulated LNCaP cell growth in a linear fashion during a 9-day observation period.

6. Effect of Fibroblast-Conditioned Medium on the Growth of LNCaP Cells in vitro To determine whether the in vivo fibroblast specificity in inducing LNCaP growth could be explained by specific soluble growth factors produced by the fibroblasts, the mitogenic activity of conditioned media from MS, rUGM, NbE-1, 3T3, CCD16, and NRK cells on LNCaP growth in vitro was compared. The conditioned media from MS, rUGM, and NbE-1 cells stimulated LNCaP cell growth up to 210% compared to controls, whereas 3T3, CCD16, and NRK conditioned media were ineffective. This paracrine effect was observed to be bidirectional, as LNCaP conditioned media stimulated rUGM cell growth up to 275% and MS cell growth 225%. The bidirectional paracrine stimulation between LNCaP and rUGM or MS cells in vitro is dependent on the concentration of conditioned media. No autocrine stimulatory effect was observed on exposing LNCaP, rUGM, or MS cells to their own conditioned media.

7. Effect of MS- and rUGM-Conditioned Media and bFGF on LNCaP Growth in vivo

Since MS- and rUGM-conditioned media and bFGF stimulated LNCaP cell growth in vitro, possible growth-promoting effects in vivo were examined following the coating of these growth factor onto a solid Gelfoam matrix. Control subcutaneous injections of Gelfoam with collagen IV plus EGF with no coinoculated LNCaP cells was found to induce local neovascularization at 3 wk, illustrating that certain growth factors could maintain their biological activity when injected subcutaneously with this technique. Coinoculation of $2 \times 10^6$ LNCaP cells with Gelfoam adsorbed with collagen IV alone or with collagen IV and EGF failed to induce LNCaP tumor formation.

However, when $2 \times 10^6$ LNCaP cells were inoculated with Gelfoam plus collagen IV adsorbed with either bFGF (1 μg/ml) or 10× concentrated conditioned media from rUGM or MS cells, LNCaP tumors formed at 60%, 50% and 38% of inoculated sites, respectively. Tumor latency, growth rate and size was similar, and did not differ from that of chimeric tumors induced by coinjecting LNCaP cells with rUGM or MS fibroblasts. Animals bearing LNCaP tumors had an elevated serum PSA (median 73 ng/ml) and the tumors were histologically carcinomas staining positive for PSA. The human prostatic origin of these tumors was confirmed with Southern dot-blot analysis for human Alu sequences and Northern analysis for PSA mRNA expression.

EXAMPLE 2

ISOLATION AND CHARACTERIZATION OF GROWTH-PROMOTING FACTOR(S) IN THE CONDITIONED MEDIA OF CULTURED HUMAN BONE STROMAL CELLS

As shown in the Example 1, accelerated LNCaP tumor growth occurred in vivo when human bone stromal cells were substituted by their conditioned media. Also, purified bFGF induced LNCaP tumor growth both in vitro and in vivo, albeit to a lesser degree. These observations prompted further studies into the properties of the conditioned media, and raised the possibility that bFGF itself may not be the most active component of the conditioned media.

The MS conditioned media was dialyzed prior to purification and analysis. Next, a sample of conditioned media was subjected to affinity chromatography using a heparin-Sepharose column. The sample was loaded onto the column in the low salt-containing buffer 10 mM Tris/HCl, 1 mM PMSF, pH 7.4, to allow binding to the column, and the column was washed with this buffer to remove any non-binding species. The components that bound to the column were eluted using the above buffer containing an increasing gradient of 0–3M NaCl. FIG. 1 compares the elution profile to the relative fraction activity of the conditioned media. Following assays of the eluted material, it was determined that the peak of the active component(s) responsible for LNCaP tumor growth in vivo corresponded to the 1M NaCl eluted fraction. This is distinct from bFGF, which is known to elute at >2.0M NaCl (Story et al., 1987). It was observed that even the trailing edge of the activity peak eluted prior to exposure to 2M NaCl. The 1M NaCl eluted active fraction from the MS conditioned media was termed MS1.

The SDS/PAGE profile of this partially purified heparin-Sepharose-eluted growth factor preparation was then determined and compared to the control media (TCM). Following silver stain analysis of SDS gels, several distinct polypeptide bands in the $M_r$ range of 18 to 228 kDa were found to be present in this fraction, which were absent from the control.

The activity of the heparin-Sepharose chromatography derived fractions in stimulating prostatic cell growth and soft-agar colony-formation, and of in vivo induction of LNCaP tumor growth were investigated. The soft agar colony formation assay is a standard in vitro assay to test for the transformation of cells, as only transformed cells can grow in an anchorage-independent manner in soft agar. Agar (0.6% (w/v)) was placed into the bottom of each well of a 24 well plate, and each well was seeded with 2,000 NbE-1 cells. A feeder layer of 0.3 to 0.4% (w/v) agar, containing the potential growth factor substances to be analyzed, was placed on top of the cells. The number of soft agar colonies formed was recorded 3 to 4 weeks after seeding. The active fractions (1M eluates) from the column were found to be particularly active in both assays, whereas control media, the 2M NaCl eluate, and similar fractions eluted by 1M NaCl from 3T3 cell conditioned media, were found to be completely inactive. Table 3 compares the results obtained using fractions obtained from the heparin-sepharose chromatographic purification step and the activity of these fractions in both in vivo and in vitro assays.

TABLE 3

| Condition | Incidence of Tumor Formation | Soft Agar Colony Formation |
|---|---|---|
| Gelfoam & Collagen IV | 0/6 (0%) | 4 ± 1.5 |
| + MS | 9/12 (75%) | 121 ± 7.2 |
| 1.0 M NaCl Eluate + MS | 0/24 (0%) | — |
| 2.0 M NaCl Eluate + 3T3 | — | 2 ± 0.7 |
| 1.0 M NaCl Eluate + TCM | 0/6 (0%) | 4 ± 0.7 |
| 1.0 M NaCl Eluate | | |

The properties of the partially purified heparin-Sepharose eluted growth factor preparation were also investigated. The mitogenic and tumor-forming activities were found to be trypsin and heat sensitive, but to be partly resistant to acid and reducing agent treatment (Table 4).

TABLE 4

| Condition | Remaining activity (%)* |
|---|---|
| None | 100 |
| Heat | |
| 70° C., 5 min | 66 ± 4 |
| 100° C., 5 min | 18 ± 3 |
| HCl, 1N | 52 ± 4 |
| Dithiothreitol (0.05 M) | 63 ± 3 |
| Trypsin (10 μg/ml) | 0 |

*Defined by [$^3$H] thymidine incorporation into cellular DNA

To quantify the purification of the bone stromal cell-derived protein factors, the specific activity of the fractions were measured. A crude conditioned medium (1400 mg) was assayed and determined to contain 60 units of activity. The anchorage-independent assay was as previously described. One unit of activity is defined as one soft agar colony stimulated by bone stromal cell-derived protein factors. The specific activity is defined as unit of soft agar colony-forming activity per mg of protein. Following the heparin-sepharose chromatography the resulting fractions were pooled and found to contain 1.3 mg of protein. The resulting protein was further fractionated by HPLC using a size exclusion column, and the resulting fractions were tested for activity. Table 5 summarizes the quantitation results of the purification of bone stromal cell-derived protein factors.

TABLE 5

| Purification Step | Total Protein (mg) | Total Activity (unit) | Specific Activity (unit/mg) | Fold Purification |
|---|---|---|---|---|
| Crude Conditioned Medium | 1400 | $8.2 \times 10^4$ | 60 | 1 |
| MS1 | 1.3 | $3.1 \times 10^5$ | 238,000 | 3,967 |
| HPLC (Size Exclusion) | 0.09 | $8.1 \times 10^4$ | 900,000 | 15,000 |

Figure 2A:
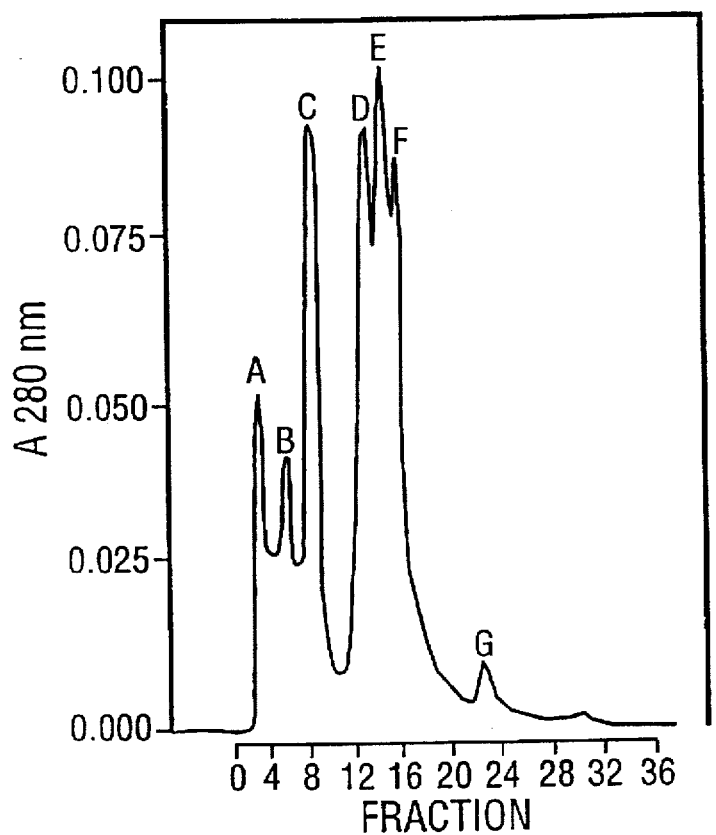
FIG. 2A. The growth-promoting fractions were pooled and were subjected to size-exclusion HPLC in which six fraction were collected, labeled A–G.
Figure 2B:
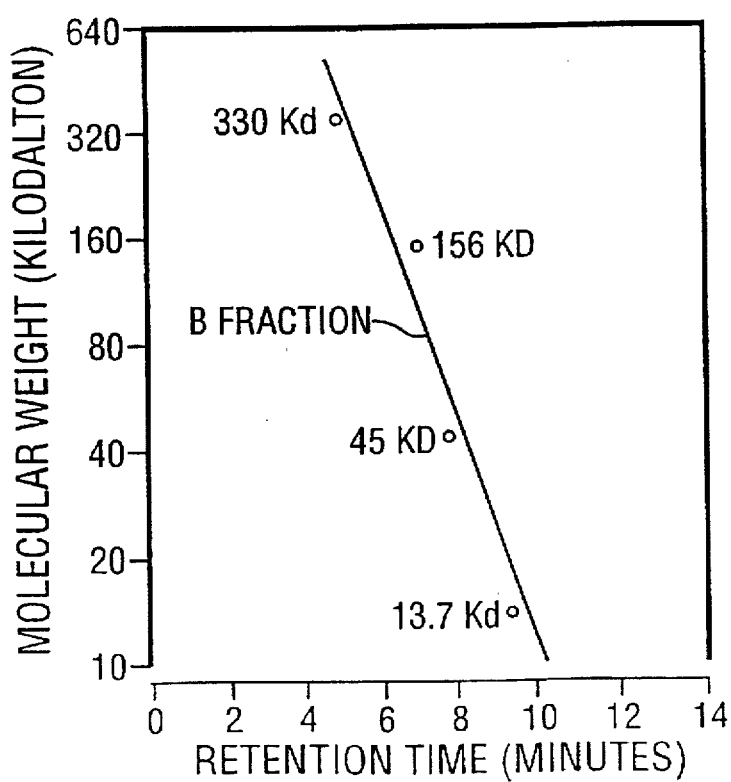
FIG. 2B. The most active fraction, B, was separated by size exclusion HPLC and found to have a molecular weight of about 220 kD, was identified to have both LNCaP tumor-inducing activity in vivo and promote anchorage-independent growth of the NbE-1 cells in vitro.
Figure 2C:
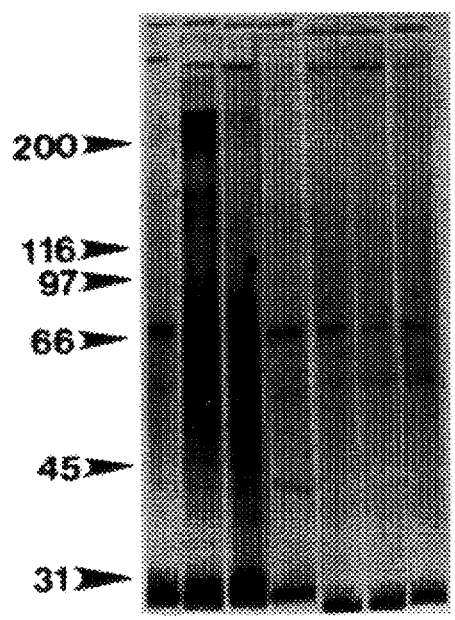
FIG. 2C. Silver stained gel of fractions A through G as shown in HPLC profile of FIG. 2A. The fractions A through G, and $P_0$ to $P_4$, can not be correlated since they are derived from different sources and during separate size fractionation. However, the growth stimulating results from both runs indicate that a high molecular weight fraction stimulates soft agar colony formation.

The growth-promoting fractions were pooled and were subjected to size-exclusion HPLC in which six fraction were collected, labeled A–G, as shown in FIG. 2A. FIG. 2B shows the determined molecular weight of the most active fraction, Fraction B, following separation by size exclusion HPLC and found to have a molecular weight of about 220 kDa, was identified to have both LNCaP tumor-inducing activity in vivo and promote anchorage-independent growth of the NbE-1 cells in vitro. Table 6 summarizes the growth promoting activity of the HPLC separated fractions, as determined in a soft agar colony formation assay.

TABLE 6

| FRACTION | NUMBER OF COLONIES PER WELL |
|---|---|
| A | 4 ± 0.6 |
| B | 49 ± 2 |
| C | 8 ± 1 |
| D | 20 ± 1.5 |
| E | 3 ± 1 |
| F | 3 ± 1.5 |
| G | 3 ± 0.5 |
| Control | 3 ± 0.5 |

FIG. 2D demonstrates by silver stain, under non-reducing conditions of SDS-PAGE separated material that within the collected fractions in this study (Fractions A–G), that the most active fraction was Fraction B which directly correlated with a molecular weight of about 220 kD by size-exclusion HPLC and by SDS-PAGE.

Figure 3:
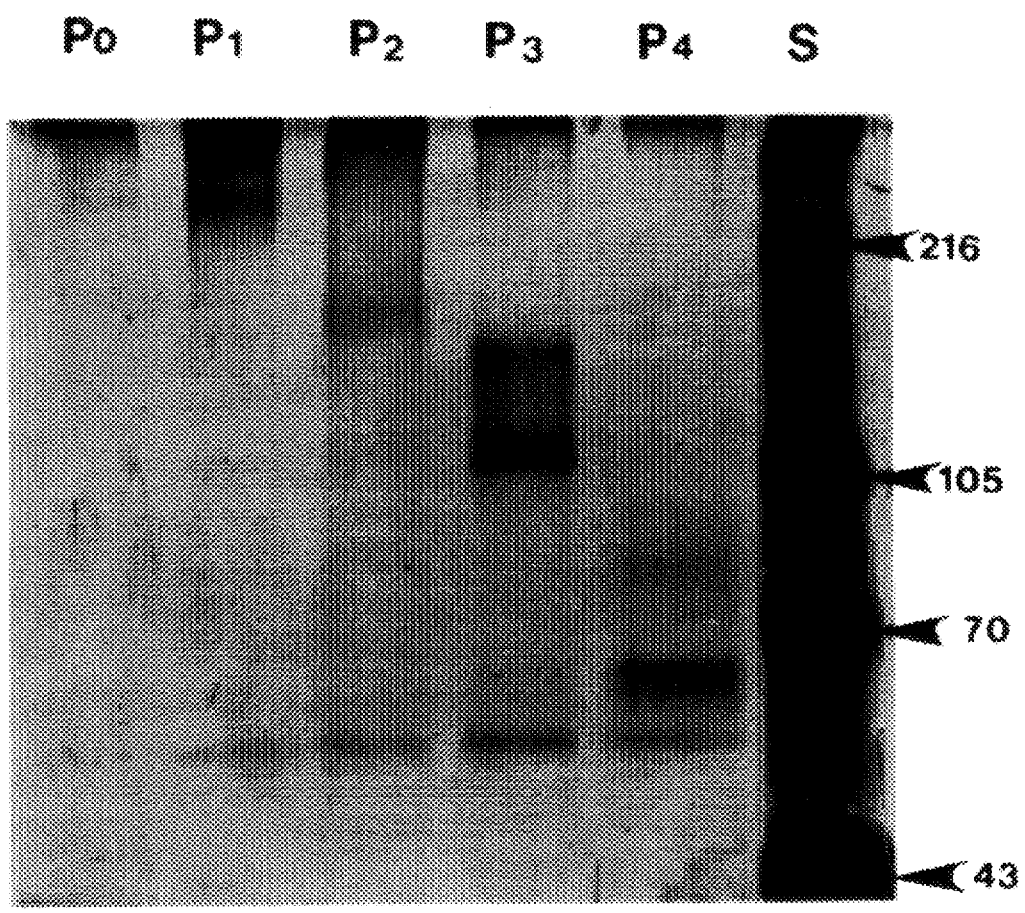
FIG. 3. SDS-PAGE under non-reducing condition in which the fractions ($P_0$ to $P_4$) have been eluted from the gel and re-run under the same non-reducing condition. The $P_1$ fraction was found to stimulate anchorage-independent prostate cell growth in vitro, an activity that was found to parallel with prostate tumor-inducing activity in vivo. Using MS-1 fraction as an antigen to immunized the mice, the inventors raised monoclonal antibodies that were screened against the combined $P_1$ and $P_2$ fractions, in order to maximize the possibility of identifying a mitogenic protein in the bone stromal conditioned medium and in human bone marrow aspirates. From a pool of monoclonal antibodies, one of such antibody, MS329, was identified that recognized specifically the P157 protein (in both bone stromal conditioned medium and in bone marrow aspirates), which also stimulates anchorage-independent prostate cell growth in vitro (as shown in FIGS. 5A and 5B below).

In a separate isolation resulting fractions following separation by heparin-Sepharose and HPLC, were further purified by separating the proteins by SDS-PAGE. The different fractions isolated are shown in FIG. 3. The resulting fractions $P_0$ to $P_4$ were electroeluted. FIG. 3 shows the fraction which were first separated by non-reducing SDS-PAGE, electroeluted, and again separated by SDS-PAGE. Electroelution was performed in 0.25M Tris/0.192M glycine pH 8.3, supplemented with 0.1% SDS, using a Bio-Rad electroeluter according to the manufacturer's instructions. The electroeluted protein was dialyzed against dd$H_2O$, containing 1 mM PMSF and used for anchorage-independent growth bioassay. Table 7 summarizes the results obtained with the electroeluted fractions on soft agar colony-forming activity induced by fractions electroeluted from SDS-PAGE.

TABLE 7

| Electroeluted Fraction | Number of Colonies Per Well |
|---|---|
| $P_0$ | 7 ± 1 |
| $P_1$ | 42 ± 4.5 |
| $P_2$ | 12 ± 1 |
| $P_3$ | 11 ± 0.5 |
| $P_4$ | 9 ± 1 |

The electroeluted fractions further identified the fraction responsible for promoting the growth of the tumor forming LNCaP cell line. This fraction contained visible proteins with an apparent molecular weight above 200 kD. However, it is, of course, generally understood by those of skill in the art that the migration of a polypeptide can vary with different conditions of SDS/PAGE (Capaldi et al., 1977) and with different sizing columns. It will therefore be appreciated that under differing electrophoretic and chromatographic conditions, the molecular weight assignments quoted above may vary.

The results of Example 1 clearly indicated that bFGF was not responsible for the growth promoting activity of the bone derived conditioned media. Further studies were conducted to confirm this observation using antibodies directed to purified growth factors. It was determined that the NbE-1 soft-agar colony-forming efficiency of the active fraction could not be inhibited using neutralizing antibodies to bFGF, KGF or HGF antibodies. Moreover, immunoblotting of the active fraction with antibodies against bFGF, KGF, TGFβ$_1$, HGF, and EGF also failed to reveal any immunoreactive bands. These results together suggest that the above factors are probably not the endogenous growth factors in the conditioned media, and therefore, that the unique growth factors of the present invention are largely responsible for such stimulatory activity.

It should be noted here that the above results do not exclude the possible involvement of factors that may belong to one of the bFGF, KGF, TGFβ, HGF, or EGF families. In another study, the inventors have also shown that bFGF, HGF, and nerve growth factor (NGF) have certain growth-promoting effects on prostate cancer cells. However, studies using antibodies against bFGF, KGF and HGF to inhibit the growth promoting activity of the MS1 fraction clearly demonstrate that the purified bone fibroblast derived prostate stimulation and growth factor is distinct. Table 8 compares the antibody mediated inhibition of soft-agar colony formation induced by MS conditioned media.

TABLE 8

| Condition | Soft Agar Colony Formation | % of Inhibition |
|---|---|---|
| EXP. 1. | | |
| Control | 9 ± 1.5 | — |
| + MS1 | 126 ± 10.1 | — |
| + MS1 & PoAb (rabbit) | 48 ± 4.3 | 66 |
| + MS1 & PoAb (mouse) | 55 ± 3.3 | 60 |
| EXP. 2. | | |
| Control | 11 ± 1.4 | — |
| + MS1 | 132 ± 15.6 | — |
| + MS1 & bFGF Ab | 109 ± 15.2 | 19 |
| + MS1 & KGF Ab | 130 ± 19.5 | 2 |
| + MS1 & HGF Ab | 128 ± 13.4 | 3 |

EXAMPLE 3

FURTHER CHARACTERIZATION OF BONE-MARROW DERIVED GROWTH FACTORS

This example demonstrates an approach which the inventors have employed in the characterization of the growth factors. The preferred approach recommended by the inventors involves the initial preparation of antibodies against the growth factor polypeptides.

To further characterize the biochemical nature of these human bone-derived growth factor(s), monoclonal antibodies (mAbs) were raised against the constituent polypeptides of fractions $P_1$ and P2 as described in Example 2. The inventors utilized the partially-purified growth factor preparation as a starting material for this procedure for the following reasons. Firstly, the action of the conditioned media cannot be neutralized using a single commercially available antibody directed against any of the known growth factors. Secondly, the total number of bone stromal cell-associated proteins in the partially purified fractions is relatively small, and it would be possible to develop specific mAbs against all of these proteins. Most importantly, fresh bone marrow supernatant fractions contain proteins similar to those of the conditioned media.

It is proposed that such mAbs have utility in a variety of different embodiments. For example, they are powerful tools for the further purification of the growth factors. Monoclonal antibodies (MAbs) against such polypeptides are therefore potentially attractive diagnostic, prognostic, imaging, and therapeutic agents for the treatment of prostate cancer in man. In that mAbs are obtained which bind specifically to the cancer cells, or to cancer-specific antigens in circulation, such mAbs would also be a powerful diagnostic agent.

The conditioned media of the MS culture was fractionated to prepare the partially purified growth factors (as described in Example 2) against which mAbs were generated. Briefly, an aliquot of this material was loaded onto a heparin-Sepharose affinity column previously equilibrated an appropriate buffer, such as Tris-HCl (pH 7.4). Proteins were eluted from the column by a continuously increasing NaCl gradient, and the concentration, mitogenic activity, and soft agar colony-forming efficiency of all fractions eluted from the column determined. The biologically active fractions were pooled and concentrated by lyophilization.

Balb/c mice of approximately 3 months in age were immunized intraperitoneally (day 0) with 10 to 50 µg/mouse of the partially purified growth factors homogenized with Ribi mouse adjuvant system (Ribi, 1985). The mice were given two consecutive weekly intraperitoneal injections of the antigens mixed with Ribi mouse adjuvant (day 7 and 14). Approximately one month after the third injection, a booster inoculation of antigens alone was given. Here the inventors contemplated the use of a novel booster method described below that was advantageously employed. The immunized mice were surgically opened to expose the spleen and a sterile solution of 5 to 20 µg of the growth factor antigens were injected directly into the spleen. The mouse was sutured and allowed to recover. This method allows for the optimal exposure of the splenocytes to the booster antigen.

Five to 7 days after the booster injection, a small amount of blood from the tail of the immunized mice was taken and tested for the presence of circulating antibodies to the growth factors by an enzyme-linked immunosorbent assay (ELISA) against immobilized fractions $P_1$ and $P_2$. Those mice producing reasonable titers of circulating antibodies to the partially purified antigens were sacrificed and their spleens aseptically removed for cell fusion.

The mouse myeloma cell line used for hybridization is the 8-azaguanine-resistant mouse murine myeloma SP2/0 non-producer cell line. The SP2/0 cell line has been selected for 8-azaguanine resistance and does not survive in medium containing hypoxanthine, aminopterin, and thymidine (HAT). The cells were fused as described (Chan et al., 1987). Immune splenocytes ($10^8$ cells) obtained from two hyper-immunized mice and 8-azaguanine-resistant SP2/0 mouse myeloma cells ($10^7$ cells) were fused using 37% (v/v) polyethylene glycol 1500 (M.W. 500–600; M.A. Bioproducts, Inc.). Fused cells were maintained for two days in growth medium that has been conditioned by SP2/0 cells, and then plated in five or six 96-well microtiter plates in growth medium containing HAT (selection medium) and screened for antibody production at the end of 2 weeks by indirect ELISA.

For the screening, purified growth factors (for isolation of the MS 329 mAb, electroeluted fractions $P_1$ and $P_2$), or partially purified growth-promoting factor(s) obtained from the conditioned media, or bone marrow supernatant fractions were used as target antigens, and media plus NaCl used as a control. The target antigens (50 ng/50 µl/well) were immobilized onto the bottoms of the 96-well microtiter plates by slow evaporation at 4° C. overnight. The culture medium from the wells propagating the splenocyte-myeloma (hybridoma) cells growing in the selection medium were assayed for secreted antibodies that react with the immobilized antigens (either bone marrow supernatant fractions, or bone stromal cell-conditioned media, or purified growth factors may be used). The isotypes of the immunoglobulin(s) produced by cloned hybridoma cell clones may be determined by ELISA, employing a commercial isotyping kit. The specificity of the mAbs was determined by reactivity with various antigens, as examined by ELISA and confirmed by western blot analysis.

The presence of a novel 157 kD growth promoting polypeptide within the active fractions was not initially detected, presumably as it was masked by an irrelevant or an inactivating polypeptide also present in the media. Its presence was shown following the generation of an anti-growth factor mAb, MS 329, which reacted with a 157 kD protein present in the active fractions and absent from the control media.

Figure 4:
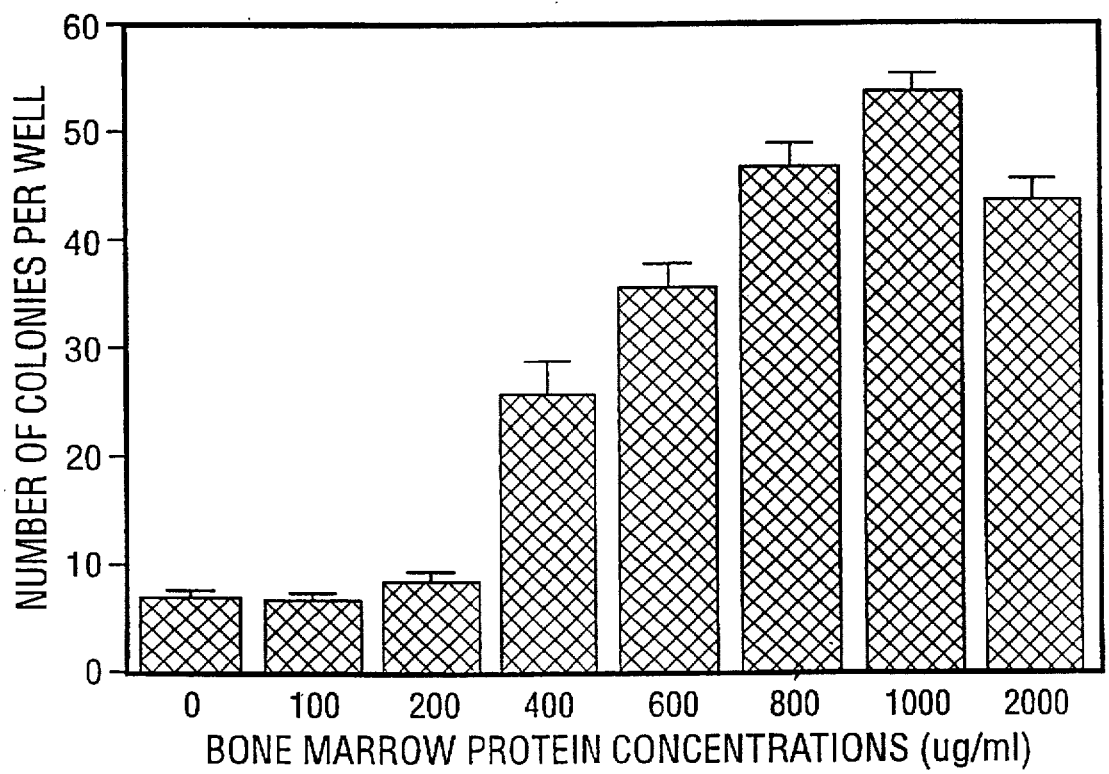
FIG. 4. Concentration dependent stimulation of soft-agar colony forming activity by a bone marrow aspirate.

To evaluate the in vivo clinical significance of the in vitro derived tumor-promoting substances, fresh human bone marrow aspirates were collected from men with prostate cancer. The aspirates were dialyzed and demonstrated concentration dependent growth promoting activity in the soft agar colony formation assay. FIG. 4 shows the concentration range that was able to stimulate anchorage-independent tumor cell growth.

Figure 5A:
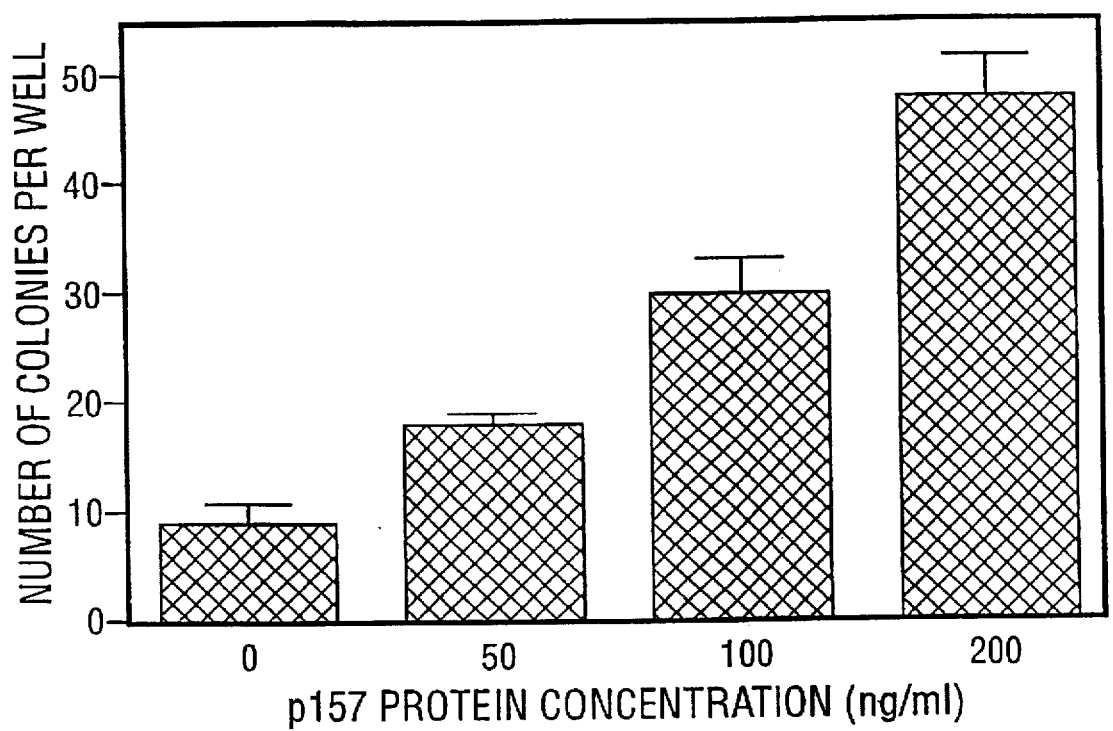
FIG. 5A. Soft-agar colony forming activity of a p157 protein purified from a bone marrow aspirate using the monoclonal antibody MS 329.
Figure 5B:
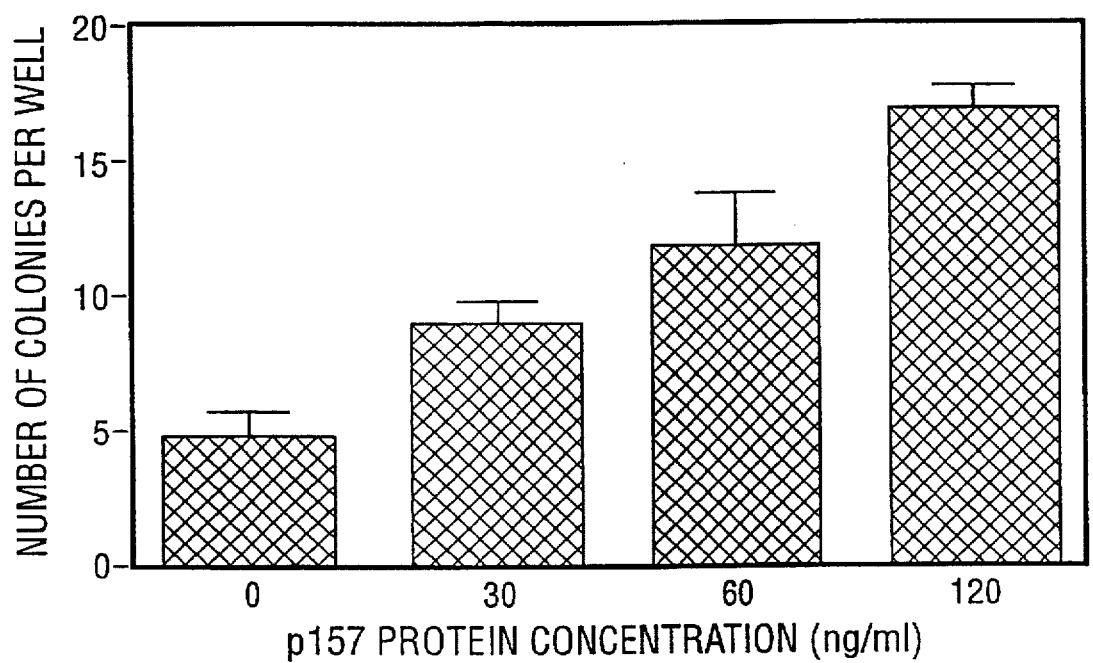
FIG. 5B. Soft-agar colony forming activity of a p157 protein purified from human bone stromal cell conditioned media using a monoclonal antibody MS 329.

The human bone marrow aspirates were further purified using an affinity purified fraction derived using ammonium sulfate precipitation, dialysis, and affinity purification of the p157 growth factor using the MS 329 mAb. FIG. 5A demonstrates the soft-agar colony formation activity range derived from the affinity purified p157 fraction, in ng/ml. To directly compare this activity, p157 was affinity purified from the conditioned media of a human bone stomal line. FIG. 5B confirms and expands the results obtained using the human bone marrow aspirate derived p157.

Following the characterization of mAbs (for example the anti-p157 clone MS 329 disclosed in the present invention) similar growth inhibiting antibodies are derived. The antibodies secreted by these clones are produced in the form of mouse ascites fluid, purified and used to antagonize the soft-agar colony-forming efficiency of NbE-1 cells which are stimulated by the partially purified growth factors. This assay is proposed to be a reproducible, convenient and rapid assay method for further characterization of novel mAbs specific for prostate cell growth factor since it is known to correlate directly with LNCaP tumorigenicity in vivo.

Using a monoclonal antibody affinity column the p157 protein was purified from both bone marrow aspirates and bone stromal cell conditioned media. The purified antigen from bone marrow aspirates and bone stromal cells was found to stimulate anchorage-independent cell growth of the prostate epithelial cells in vitro.

EXAMPLE 4

ISOLATION OF PSAF

Figure 6A:
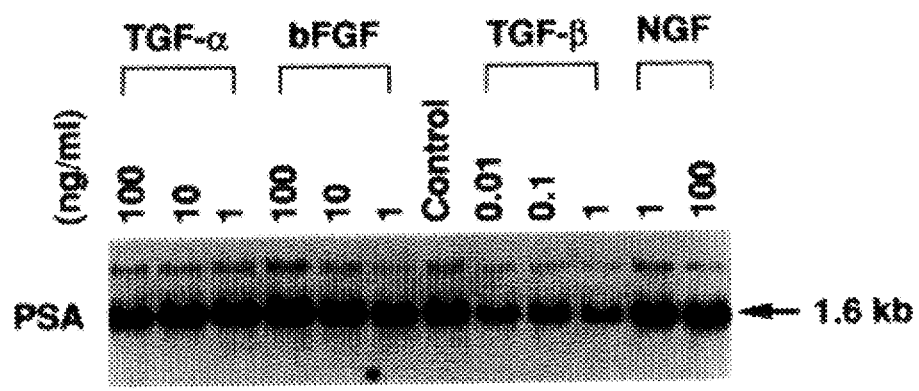
FIG. 6A. The effect of PSA gene expression in parental LNCaP cells treated with a variety of growth factors. The parental LNCaP cells were incubated with agents as indicated (control cells were incubated with T medium containing 2% TCM). Forty-eight hours after treatment, total cellular RNA was prepared and 20 µg of total cellular RNA was subjected to Northern analysis. Relative PSA mRNA levels (in parenthesis) were determined by densitometrical quantification, and the control is defined as 1.0; (A) TGF-α 100 (0.98); TGF-α 10 (1.01); TGF-α 1 (1.15); bFGF 100 (1.22); bFGF 10 (1.04); bFGF 1 (0.97); TGF-β 0.01 (0.72); TGF-β 0.1 (0.84); TGF-β 1 (0.53); NGF 1 (1.13); NGF 100 (1.08).
Figure 6B:
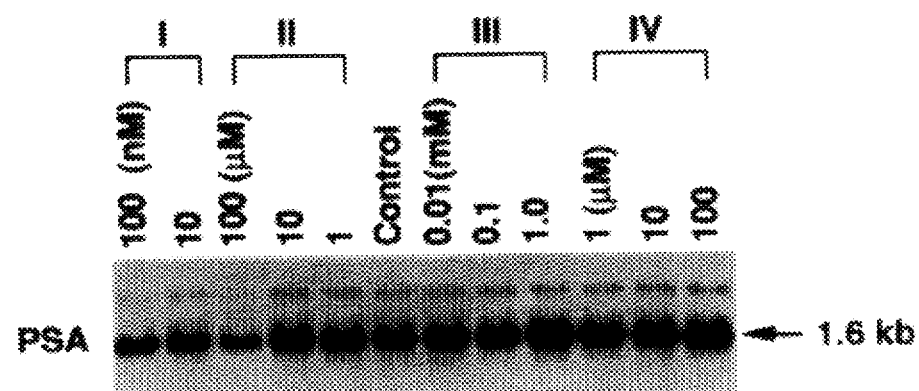
FIG. 6B. The effect of PSA gene expression in parental LNCaP cells treated with a neuropeptide and a variety of α1 and β2-adrenergic agonists. I. bombesin 100 (0.62); bombesin 10 (0.89); II. isoproterenol 100 (0.51); isoproterenol 10 (1.11); isoproterenol 1 (1.07); III. dibutyryl cAMP 0.01 (1.09); dibutyryl cAMP 0.1 (1.11); dibutyryl cAMP 1.0 (1.23); IV. phenylephrine 1 (1.10); phenylephrine 10 (1.08); phenylephrine 100 (1.14).

As LNCaP cells became progressively androgen-refractory, the inventors noted that the androgen-independent LNCaP sublines secreted PSAF which promotes PSA synthesis and secretion by LNCaP cells (Chung (1993), and Hsieh, et al. (1993)). To further examine the biochemical nature of the PSAF, the effect of the fractions on PSA mRNA expression levels were examined. Various known factors within the optimal concentration of growth stimulation for LNCaP and other cell types were examined for their PSAF activity. Results of these studies showed that no apparent increases in the steady-state levels of PSA mRNA can be detected in the parental LNCaP cells in the presence of growth factors such as, TGF-α, TGF-β, bFGF, NGF, HGF and KGF, neuropeptides (bombesin/GRP), second messenger analogue (dibutyryl cAMP), α1-adrenergic agonist (phenylephrine), and β2-adrenergic agonist (isoproterenol) (FIGS. 6A and 6B). These studies indicate that the nature of the prostate cell-derived PSAF differs from these known growth factors, neurotransmitters, and that the induction may not be elicited through signal transduction pathways mediated by androgen receptor (AR), protein kinase C, or protein kinase A.

PSA mRNA levels were also examined using partially purified growth promoting factor(s) from CM of the C4 Subline. To characterize the action of prostate cell growth factor on upregulating PSA mRNA, parental LNCaP cells were incubated with 2-fold concentrated CM from C4 subline for various periods. The CM was removed at the end of incubation period, and the cells were changed to serum-free medium and assayed at 48 hours post-treatment.

Figure 7A:
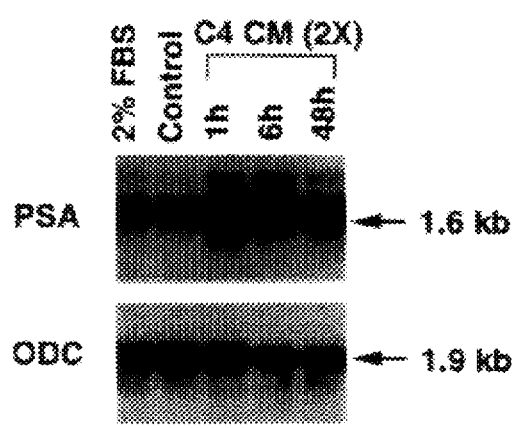
FIG. 7A. Partial characterization of partially purified PSAF (PSA Stimulatory Autocrine/actor) produced by the C4 subline. Two times concentrated conditioned medium (CM) from C4 subline was incubated with parental LNCaP cells at the indicated time; then cells were washed with PBS and replaced with fresh T medium containing 2% CM. The steady-state levels of PSA and ODC mRNA were determined 48 h after treatment.
Figure 7B:
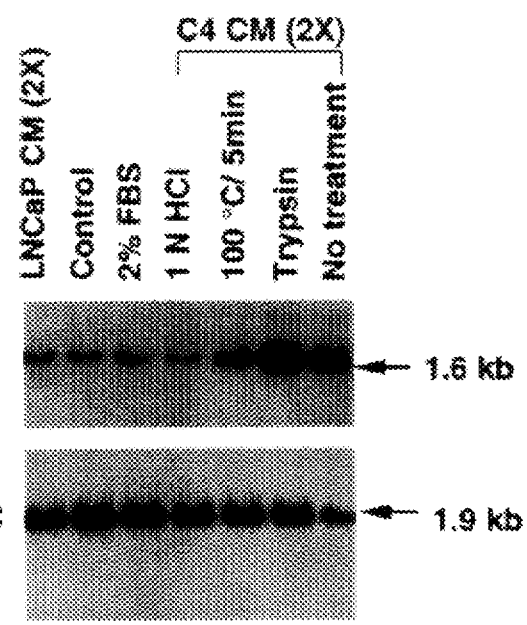
FIG. 7B. Partial characterization of PSAF produced by the C4 subline. Two times concentrated CM from C4 subline was treated with 1N HCl (4° C., overnight), then neutralized with 10N NaCl to pH 7.5 and dialyzed; or heated at 100° C. (5 min); or digested with trypsin (10 mg/ml, 37° C., 2 h), then neutralized with trypsin inhibitor before adding into parental LNCaP cells. The parental LNCaP cells were washed with PBS and replaced with fresh T medium containing 2% TCM. The steady-state levels of PSA and ODC mRNA were determined 48 h after treatment.
Figure 7C:
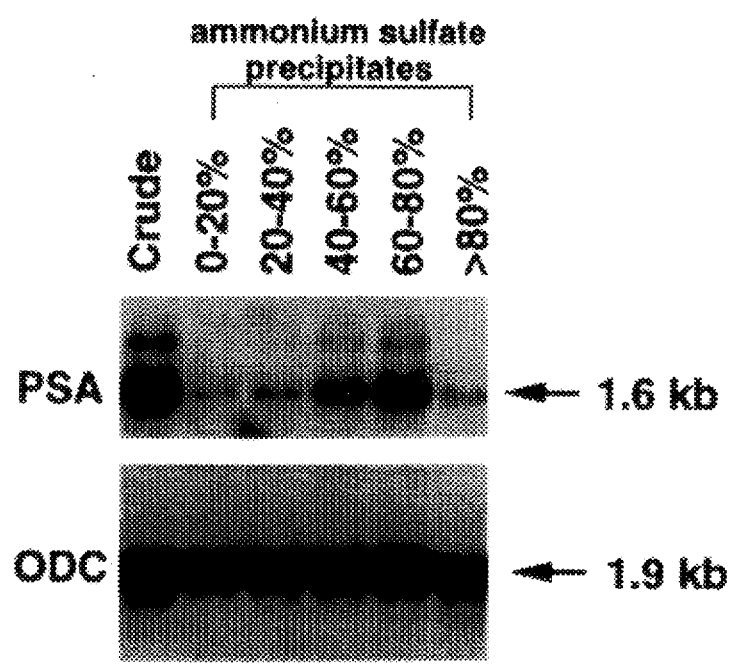
FIG. 7C. Partial characterization of PSAF produced by the C4 subline. CM from C4 subline was precipitated with ammonium sulfate at the indicated concentrations, each fraction was dialyzed with a 3,500 molecular weight cut-off membrane against distilled water for 24 h and concentrated by lyophilizer. The same protein content (900 µg) from each fraction and crude were incubated with parental LNCaP cells for 48 h. The parental LNCaP cells were washed with PBS and replaced with fresh T medium containing 2% TCM. The steady-state levels of PSA and ODC mRNA were determined 48 h after treatment.

Northern blot analysis of PSA mRNA revealed that a short term exposure (1 hour) of C4 CM to parental LNCaP cells is sufficient to elicit the signal(s) necessary to increase the steady-state levels of PSA mRNA when determined at 48 hours (FIG. 7A). The active PSA-inducing factor was tested by standard biochemical methods as shown in FIG. 7B, prostate cell-derived PSAF was sensitive to heat and acid treatment, but was resistant to trypsin digestion. Furthermore, the majority of prostate cell-derived PSAF activity is still retained in the 60–80% of ammonium sulfate fraction (FIG. 7C). These result indicate that prostate cell-derived PSAF can induce increased expression of PSA steady state mRNA, and this inducing activity is resistant to trypsin-mediated protease digestion because of its amino acid composition.

That PSAF was capable of increasing steady state PSA mRNA levels was surprising, since current knowledge indicated that PSA mRNA levels were solely regulated by androgen. The regulation of PSA expression by PSAF, particularly in androgen-refractory human prostate cancer, will have profound clinical value in the diagnosis, prognosis, and treatment of androgen-independent hormonally-refractory, human prostate cancer.

EXAMPLE 5

USING MONOCLONAL ANTIBODIES FOR DIAGNOSIS OF HUMAN PROSTATE CANCER METASTASIS

The inventors further propose that the present invention will allow one of skill in the art to identify specific mAbs that will have diagnostic and prognostic values in predicting human prostate cancer metastasis to the bone, imaging the prostatic metastasis, and inhibiting tumor-stromal interaction. The criteria to be used in assaying for such mAbs are proposed to include tests for, e.g., specific reaction with a defined protein band of conditioned media in immunoblots or in immunohistochemical assays; and/or competition for the binding of the putative growth promoting factor(s) with the cell membrane fraction prepared from prostate cancer cell lines.

Once specific mAb(s) that meet the above criteria have been identified, the inventors contemplate their use in diagnosis, prognosis, imaging, and therapy. This approach is advantageous because, unlike any anti-PSA antibodies, the mAbs against cancer-specific antigens may not be trapped in the blood compartment and they would therefore more efficiently block prostate cancer and bone cellular interactions.

In addition, the inventors propose that the levels of these growth factors may correlate positively with prostate cancer progression, as was found in the mouse-human tumorigenicity model system. To investigate this, it is proposed that bone marrow aspirates be obtained initially from late stages of the untreated prostate cancer patients (Stage D1, D2) and prostate cancer patients treated with hormonal therapy, or failed hormonal therapy, and chemotherapy. The concentration of growth factors in such samples be analyzed by ELISA, or radioimmunoassay (RIA) and compared to the number of prostate cancer cells present in bone marrow using the monoclonal antibodies of the present invention.

The inventors propose that the concentrations of growth factors will correlate with the proliferative potential and aggressiveness of the prostate tumor in vivo and inversely with patients' survival, and may predict the length of period of remission and disease-free survival. The concentration of these growth factors will also serve as a valuable index to predict cancer progression prior to the manifestation of clinical symptoms. It is believed that the ELISA or RIA assay contemplated by the inventors will be extremely sensitive. Based on immunoblot analysis of the growth factors, the sensitivity of this assay is estimated to be in the nanogram range. This sensitivity of assay could be used effectively to diagnose prostate cancer, or to predict the progression of prostate cancer and its response to various therapies in very small volumes of bone marrow aspirates. Similarly, the assay will be refined as a diagnostic tool for the early detection of the onset of prostate cancer.

EXAMPLE 6

USE OF ANTI-GROWTH FACTOR MONOCLONAL ANTIBODIES FOR RADIO IMAGING

The monoclonal antibodies of this invention will be used to quantify and localize the expression of the prostate cell growth factor(s). The anti-p157 monoclonal antibody, for example, will be labeled by a variety of methods and used to visualize the localized concentration of the cells producing the growth factor as well as the cells that contain the growth factor receptor.

It is proposed that the mAb(s) will have utility in radio-imaging protocols. mAb(s) labeled with indium-111 can be administered to mice previously inoculated with LNCaP and bone fibroblasts for the development of LNCaP tumors. In this manner the tumor can be imaged, the sensitivity determined, and the distribution of mAb-$^{111}$In complex in this experimental model of prostate cancer examined. mAb (s) previously labeled with [$^{131}$I] or mAb-immunotoxins such as mAb-ricin A chain (Pearson et al., 1990) could be delivered through continuous infusion to mice which bear experimental LNCaP tumors and the outcome monitored.

For example, the anti-p157 protein mAb MS329 may be linked to a toxin, e.g., exotoxin, by means well known in the art, and contacted with cells. The p157 mAb-exotoxin conjugate being cytotoxic to said cells, wherein the cells are susceptible to the toxin. The inventors have applied this general method recently for the treatment of human bladder carcinoma in vitro, and have observed some encouraging results (Gleave et al., Cancer Res. 53:5300–5307, 1993).

It will be apparent to those of skill in the art that a similar approach may be used to radio-image the production of the growth factor in human patients.

EXAMPLE 7

PURIFICATION OF THE GROWTH FACTOR

The specific mAbs are employed in the rapid purification of the growth factor polypeptides following the creation of a mAb-affinity column. This can be achieved by conjugating a specific mAb to cyanogen bromide (CNBr)-activated sepharose CL4B (Pharmacia) (Chan et al., 1986; Li et al., 1987) or a similar solid support matrix. As such, the antibodies are first attached to CNBr-sepharose, and the antisera-bound matrix poured into a column and washed with a suitable wash buffer. An aqueous mixture including the growth factor polypeptides is passed over the column under conditions to allow for immunocomplex formation between components in the mixture and the sepharose-bound antibodies. The column is washed extensively to remove non-specifically bound material and the specifically-bound antigens eluted from the column in a substantially purified state.

A solid support matrix for use in affinity chromatography is understood by those of skill in the art to be a specific and rapid means of significantly purifying an antigen. Briefly, affinity chromatography is based on the recognition of a protein by a substance such as a ligand or an antibody. The column material is synthesized by covalently coupling a binding molecule, such as a protein, for example to an insoluble matrix. The column material is then allowed to adsorb the desired substance from solution and then the conditions are changed to those under which binding does not occur and the substrate is eluted. The requirements for successful affinity chromatography are that the matrix must adsorb molecules, the ligand must be coupled without altering its binding activity, a ligand must be chosen whose binding is sufficiently tight, and it must be possible to elute the substance without destroying it.

Often, the ligand which is immobilized is a protein which binds a substance, in this case a monoclonal antibody, e.g., MS 329 that recognizes a prostate growth factor protein. Various materials are available for immobilizing ligands. In addition to cyanogen bromide activated agarose, other examples include but are not limited to; 6-aminohexanoic acid and 1,6 diaminohexane-agarose, epoxy-activated agarose, thiopropyl agarose, carbonyldiimidazole activated agarose, and aminoethyl and hydrazide activated polyacrylamide (See for example Physical Biochemistry, David Freifelder ed., 2nd edition, Freeman and Company, San Francisco, Calif., 1982).

The purified growth factor(s) are also useful in inhibition studies analyzing the effects of prostate specific growth factor in cells or animals. Anti-growth factor antibodies are useful in immunolocalization studies to analyze the distribution of the growth factor ligand during various cellular events, for example, to determine the effects of ligand binding on the cell membrane. Furthermore, the activation effects of the growth factor can be studied in the presence or absence of androgens. A particularly useful application of such antibodies is in purifying native or recombinant p157, for example, using an antibody affinity column. The operation of all such immunological techniques will be known to those of skill in the art in light of the present disclosure.

Such an affinity column can also be used to isolate and characterize growth-promoting component(s) from human bone marrow aspirates obtained from prostate cancer patients. In such embodiments, bone marrow aspirates (~10 ml per patient, at 20 to 30 mg protein/ml) are obtained from prostate cancer patients, from female breast cancer patients (with or without bony metastasis), and from healthy normal male and female donors and analyzed. From such investigations, the sex-dependent differences and disease specificity of the growth factors that appear to promote human prostate tumor growth are also investigated.

PROPHETIC EXAMPLE 8

MOLECULAR CLONING AND EXPRESSION OF THE GROWTH FACTORS

In general, both poly- and monoclonal antibodies against the prostate cell growth factor(s) are used in a variety of embodiments. For example, the mAbs can be employed in antibody directed cloning protocols to obtain cDNAs or genes encoding the growth factor or related proteins.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., obtaining a specific DNA molecule distinct from other portions of DNA. This can be achieved by, for example, cloning a cDNA molecule, or cloning a genomic-like DNA molecule. Techniques such as these would also, of course, be appropriate for the production of the p157 protein, and other proteins in the prostate cell stimulating fractions derived during the purification of the growth factor(s) in accordance with the present invention.

The first step in such cloning procedures is the screening of an appropriate DNA library, such as, in the present case, a bone marrow-derived library. The screening procedure may be an expression screening protocol employing the monoclonal antibodies directed against the p157 protein, or activity assays. Alternatively, screening may be based on the hybridization of oligonucleotide probes, designed from a consideration of portions of the amino acid sequence of the protein. After identifying an appropriate DNA molecule, it may be inserted into any one of the many vectors currently known in the art and transferred to a prokaryotic or eukaryotic host cell where it will direct the expression and production of the so-called recombinant version of the protein.

Turning firstly to the expression of the prostate cell growth factor. Once a suitable (full length if desired) clone or clones have been obtained, whether they be cDNA based or genomic, one may proceed to prepare an expression system for the recombinant preparation of the growth promoting protein. The engineering of DNA segment(s) for expression in a prokaryotic or eukaryotic system may be performed by techniques generally known to those of skill in recombinant expression. It is believed that virtually any expression system may be employed in the production of the growth factor protein encoded by the isolated DNA segment.

The prostate growth factor may be successfully expressed in eukaryotic expression systems with the production of active post-translationally processed factor, however, it is envisioned that bacterial expression systems may ultimately be preferred for the preparation of prostate growth factor for all purposes. The cDNA for the growth factor may be separately expressed in bacterial systems, with the encoded proteins being expressed as fusions with β-galactosidase, maltose-binding protein, avidin, ubiquitin, Schistosoma japonicum glutathione S-transferase, and the like. It is believed that bacterial expression will ultimately have numerous advantages over eukaryotic expression in terms of ease of use and quantity of materials obtained thereby.

It is proposed that transformation of host cells with DNA segments encoding the isolated prostate growth factor encoding protein will provide a convenient means for obtaining active factor. However, separate expression followed by reconstitution is also certainly within the scope of the invention. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of the growth factor, e.g., baculovirus-based, glutamine synthase-based or dihydrofolate reductase-based systems could be employed. For example, plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the enzyme, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

As noted above, it is proposed that in embodiments concerning the production of more than one prostate growth factor it may be co-expressed in the same cell. This may be achieved by co-transfecting the cell with two distinct recombinant vectors, each bearing a copy of either of the growth factor-encoding DNA. Alternatively, a single recombinant vector may be constructed to include the coding regions for both factors, which could then be expressed in cells transfected with the single vector. In either event, the term "co-expression" herein refers to the expression of both factors in the same recombinant cell.

It is contemplated that virtually any of the commonly employed host cells can be used in connection with the expression of the prostate growth factors in accordance herewith. Examples include cell lines typically employed for eukaryotic expression such as 239, AtT-20, HepG2, VERO, HeLa, CHO, WI 38, BHK, COS-7, RIN and MDCK cell lines.

It is contemplated that the growth factor of the invention may be "overexpressed", i.e., expressed in increased levels relative to its natural expression in prokaryotic or eukaryotic cells, or even relative to the expression of other proteins in the recombinant host cell. Such overexpression may be assessed by a variety of methods, including radio-labelling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural bone marrow cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a prostate specific growth factor has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

Engineered cells of the present invention will generally be derived from a cell line comprised of cells capable of forming secretory granules. Secretory granules are generally confined to mammalian cells whose main function is the synthesis and secretion of peptides. Generally speaking, secretory granules are found in endocrine cells. Secretory granules are formed by budding of intracellular membranous structures known as the Golgi apparatus. The important and unique features of this system are 1) the secretory granules allow a supply of a particular hormone or growth factor to be built up and stored for release at the time when it is needed to perform its function and 2) the presence of processing enzymes in the granules allow efficient conversion of the precursor forms of hormones or growth factors to the mature forms.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventor has noticed that the level of expression from the introduced gene(s) of interest can vary in different clones, probably as a function of the site of insertion of the recombinant gene in the chromosomal DNA. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for the cell type used for engineering, such as the insulin promoter in insulinoma cell lines, the prolactin or growth hormone promoters in anterior pituitary cell lines, the PSA or Probasin promoter for directing the expression of the steady state levels of androgen-induced genes (or androgen repressed genes) in prostate cells.

A separate approach is to overexpress PSAF in prostate cells with varying tumorigenic and metastatic potential. In this way the specific biologic activity of PSAF is isolated from prostate cells. Since PSAF induces PSA expression and PSA is a serine protease which has been proposed to process growth factor proteins from their inactive to active state, it is potentially possible that PSAF may regulate growth by indirectly processing growth factors. In addition, PSA has also been shown to exhibit direct growth-promoting effects on cells in culture.

It will be understood that the recombinant growth factor (s), such as PSAF, may differ from naturally-produced growth factor in certain ways. In particular, the degree of post-translational modifications, such as, for example, glycosylation and phosphorylation may be different between the recombinant protein and the protein purified from a natural source, such as the conditioned medium or the bone marrow cell aspirates.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Batson, O. V. The function of the vertebral veins and their role in the spread of metastasis. Ann. Surg. 112:138–149, 1940.

Berrettoni, B. A., and J. R. Carter. Mechanisms of cancer metastases to bone. J. Bone J. Surg. Am. 68A:308–312, 1986.

Camps, J. L., S. M. Chang, T. C. Hsu, M. R. Freeman, S. J. Hong, H. E. Zhau, A. C. von Eschenbach, and L. W. K. Chung. Fibroblast-mediated acceleration of human epithelial tumor growth in vivo. Proc. Natl. Acad. Sci. 87:75–79, 1990.

Canalis, E., T. McCarthy, and M. Centrella. Isolation and characterization of insulin-like growth factor I (somatomedin-C) from cultures of fetal rat calvariae. Endocrinology 122:22–27, 1988.

Capaldi et al., Biochem. Biophys. Res. Comm., 76:425, 1977.

Carter, H. B.,and D. S. Coffey. The prostate: An increasing medical problem. The Prostate 16:39–48, 1990.

Chackel-Roy, M., C. Niemeyer, M. Moore, and B. R. Zetter. Stimulation of human prostatic carcinoma cell growth by factors present in human bone marrow. J. Clin. Invest. 84:43–50, 1989.

Chan, J. C., Keck, M. E., and Li, W. J. Biochem. Biophys. Res. Comm. 134:1223–1230, 1986.

Chang, S. M., and Chung, L. W. K. Interaction between prostatic fibroblast and epithelial cells in culture: Role of androgen. Endocrinology 125:2719–2727, 1989.

Chi, K. C., Scanlon, M. D., Henkel, R., Dreesman, G., Seo, J. S., Bowen, J. M. and Chan, J. C. Detection of human plasma-associated hepatitis (MAb): The same MAb can be used as both capture and tracer antibody. Diagnosis & Clin. Immunol. 5:91–99, 1987.

Chomcjymski, P., and N. Sacchi. Single step method of RNA isolation by acid guanidinium thiocyanate-phenol-chloroform extraction. Anal. Biochem. 162:156–159, 1987.

Chung, L. W. K., J. Matsura, and M. N. Runner. Tissue interaction and prostatic growth. I. Induction of adult mouse prostatic hyperplasia by renal urogenital sinus implants. Biol. Reprod. 31:155–163, 1984.

Chung, L. W. K., S. M. Chang, C. Bell, H. E. Zhau, J. Y. Ro, and A. C. von Eschenbach. Coinoculation of tumorigenic rat prostate mesenchymal cells with nontumorigenic epithelial cells results in the development of carcinosarcoma in syngeneic and athymic animals. Int. J. Cancer 43:1179–1187, 1989.

Cook, G. B., and F. R. Watson. Events in the natural history of prostate cancer: Using salvage curve, mean age distributions, and contingency coefficients. J. Urol. 99:87–91, 1968.

Cunha, G. R., and L. W. K. Chung. Stromal-epithelial interactions: I. Induction of prostatic phenotype in urothelium of testicular feminized (Tfm/y) mice. J. Steroid Biochem. 14:1317–1321, 1981.

Davis, L. G., M. D. Dibner, and J. E. Battery. Rapid DNA preparation. In: Basic Methods in Molecular Biology. Elsevier Science Publishers, New York, 42–43, 1986.

DeCosse, J., C. L. Gossens, and J. F. Kuzma. Breast cancer: Induction of differentiation by embryonic tissue. Science 181:1057–1058, 1973.

Dedhar, S. Integrins and tumor invasion. Bioessays. 12:583–590, 1990.

Dickson, R. B., M. E. McManaway, and M. E. Lippman. Estrogen-induced factors of breast cancer cells partially replace estrogen to promote tumor growth. Science. 232:1540–1543, 1986.

Drewinko, B., Yang, L. Y., Chan, J. C., and Trujillo, J. M. New monoclonal antibodies against colon-cancer-associated antigens. Cancer Res. 46:5137–5143, 1986.

Elkin, M., and H. P. Mueller. Metastases from cancer of the prostate: Autopsy and roentgenological findings. Cancer 7:1246–1248, 1979.

Ensoli, B., S. Nakamura, S. Z. Salahuddin, P. Biberfeld, L. Larsson, B. Beaver, F. Wang-Staal, and R. C. Gallo. AIDS-Kaposi's sarcoma-derived cells express cytokines with autocrine and paracrine growth effects. Science 243:223–226, 1989.

Fidler, I. J., and G. L. Nicolson. Organ selectivity for implantation, survival and growth of B16 melanoma variant tumor lines. J. Natl. Cancer Inst. 57:1199–1202, 1976.

Ford, T. F., D. N. Butcher, J. R. W. Masters, and M. C. Parkinson. Immunocytochemical localization of prostate-specific antigen: Specificity and application to clinical practice. Br. J. Urol. 57:50–55, 1985.

Frank, L. M., P. N. Riddle, A. W. Carbonell, and G. O. Gey. A comparative study of the ultrastructure and lack of growth capacity of adult human prostate epithelium mechanically separated from its stroma. J. Pathol. 100:113–119, 1970.

Franks, L. M. The spread of prostatic carcinoma. J. Pathol. 73:603–611, 1956.

Gillies, R. J., N. Didier, and M. Denton. 1986. Determination of cell number in monolayer cultures. Anal. Biochem. 159:109–113, 1987.

Gleave et al., Cancer Res. 53:5300–5307, 1993.

Globus, R., J. Plouet, and D. Gospodarowicz. Cultured bovine bone cells synthesize basic fibroblast growth factor and store it in their extracellular matrix. Endocrinology 124:1539–1547, 1989.

Guthrie, P. D., Freeman, M. R., Liao, S., and Chung, L. W. K. Regulation of gene expression in rat prostate by androgen and $\beta$-adrenergic receptor pathways. Mol. Endocrinol. 4:1343–1353, 1990.

Hart, I. R. "Seed and soil" revisited: Mechanisms of site-specific metastasis. Cancer Metastasis Rev. 1:5–16, 1985.

Hauschka, P. V., A. E. Mavrakos, M. D. Iafrati, S. E. Soleman, and M. Klagsbrun. Growth factors in bone matrix: Isolation of multiple types by affinity chromatography on heparin Sepharose. J. Biol. Chem. 261:12665–12674, 1986.

Hodges, G. M., R. M. Hicks, and G. D. Spacey. Epithelial-stromal interactions in normal and chemical carcinogen-treated adult bladder. Cancer Res. 37:3720–3730, 1977.

Horak, E., D. Z. Darling, and D. Tarin. Organ specific effects on metastatic tumour growth studied in vitro. In: Treatment of Metastasis: Problems and Prospects. K. Hellman and S. A. Eccles, editors. Taylor and Francis, London. 369–372, 1985.

Horoszewicz, J. S., S. S. Leong, E. Kawinski, J. P. Kerr, H. Rosenthal, T. M. Chu, E. A. Mirand, and G. P. Murphy. LNCaP model of human prostatic carcinoma. Cancer Res. 43:1809–1818, 1983.

Hujanen, E. S., and V. P. Terranova. Migration of tumor cells to organ-derived chemoattractants. Cancer Res. 45:3517–3521, 1985.

Isaacs, J. T. Development and characteristics of available animal model systems for the study of prostate cancer. In: Current Concepts and Approaches to the Study of Prostate Cancer. D. S. Coffey, W. A. Gardner, Jr., N Bruchovsky, M. I. Resnick, and J. P. Karr, editors. Alan R. Liss, New York. 513–576, 1987.

Jacobs, S. C. Spread of prostatic carcinoma to bone. Urology 21:337–344, 1983.

Jacobs, S. C, D. Pikna, and R. K. Lawson. Prostatic osteoblastic factor. Invest. Urol. 17:195–198, 1979.

Janek, P., P. Briand, and N. R. Hartman. The effect of estrone-progesterone treatment on cell proliferation kinetics of hormone-dependent GR mouse mammary tumors. Cancer Res. 35:3698–3704, 1975.

Johnson, D. E. Cancer of the prostate: Overview. In: Genitourinary Tumors: Fundamental Principles and Surgical Techniques. D. E. Johnson, and M. A. Boileau, editors. Grune and Stratton, Inc., New York. 1–31, 1982.

Kabalin, J. N., D. M. Peehl, and T. A. Stamey. Clonal growth of human prostatic epithelial cells is stimulated by fibroblasts. The Prostate 14:251–263, 1989.

Kanamarus, H., and O. Yoshida. Assessment of in vitro lymphokine activated killer (LAK) cell activity against renal cancer cell lines and its suppression by serum factor using crystal violet assay. Urol. Res. 17:259–264, 1989.

Kratochwil, K. Tissue interactions during embryonic development. In: Tissue Interactions in Carcinogenesis. D. Tarin, editor. Academic Press, London. 1–47, 1972.

LaRocca, R. V., Stein, C. A. and Myers, C. E. Cancer Cells 2:106–115, 1990.

Li, W. J., Chi, K., Gallick, G., and Chan, J. C. Virology 156:91, 1987.

Lu, J., Y. Nishizawa, A. Tamaka, N. Nonomura, H. Yamanishi, N. Uchida, B. Sato, and K. Matsumoto. Inhibitory effect of antibody against basic fibroblast growth factor on androgen- or glucocorticoid-induced growth of Shionogi carcinoma 115 cells in serum-free culture. Cancer Res. 49:4963–4967, 1989.

Lundwall, A., and H. Lilja. Molecular cloning of human prostate specific antigen cDNA. FEBS Lett. 214:317–322. 1987

Manishen, W. J., K. Sivananthan, and F. W. Orr. Resorbing bone stimulates tumor cell growth: A role for the host microenvironment in bone metastasis. Am. J. Pathol. 123:39–45, 1985.

Miller, F. R., D. McEachern, and B. E. Miller. Growth regulation of mouse mammary tumor cells in collagen gel cultures by diffusible factors produced by normal mammary gland epithelium and stromal fibroblasts. Cancer Res. 49:6091–6097, 1989.

Mundy, G. R., S. DeMartino, and D. W. Rowe. 1981. Collagen and collagen-derived fragments are chemotactic for tumor cells. J. Clin. Invest. 68:1102–1105, 1982.

Mydlo, J. H., J. Michaeli, W. D. W. Heston, and W. R. Fair. Expression of basic fibroblast growth factors mRNA in benign prostatic hyperplasia and prostatic carcinoma. The Prostate. 13:241–247, 1988.

Nicolson, G. L., and J. L. Winkelhake. Organ specificity of blood-born tumour metastasis determined by cell adhesion. Nature 255:230–232, 1975.

Nicolson, G. Cancer metastasis. Sci. Am. 240:66–76, 1979.

Nishi, N., Y. Matuo, K. Kunitomi, I. Takenaka, M. Usami, T. Kotake, and F. Wada. Comparative analysis of growth factors in normal and pathologic human prostates. The Prostate 13:39–48, 1988.

Nonomura, N., N. Nakamura, N. Uchida, S. Noguchi, B. Sato, T. Sonoda, and K. Matsumoto. Growth-stimulating effect of androgen-induced autocrine growth factor(s) secreted from Shionogi carcinoma 115 cells on androgen-unresponsive cancer cells in a paracrine mechanism. Cancer Res. 48:4904–4908, 1988.

Paget, S. The distribution of secondary growths in cancer of the breast. Lancet 1:571–573, 1989.

Papsidero, L. D., M. Kuriyama, M. L. Wang, J. S. Horoszewicz, S. S. Leong, L. Valenzuela, G. P. Murphy, and T. M. Chu. Prostate antigen: A marker for human prostate epithelial cells. J. Natl. Cancer Inst. 66:37–42, 1981.

Pearson, J. W. Hedrick, E., Fogler, W. E., Bull, R. L., Ferris, D. K., Riggs, C. W., Wiltrout, R. H., Sivan, G., Morgan, A. C., Groves, E. and Longo, D. L. Cancer Res. 50:6379–6388, 1990.

Perkel, V. S., Mohan, S., Herring, S. J., Baylik, D. J., and Linkhart, T. A. Human prostate cancer cells, PC3, elaborate mitogenic activity which selectively stimulates human bone cells. Cancer Res. 50:6902–6907, 1990.

Picard, O., Y. Rolland, and M. F. Poupin. Fibroblast-dependent tumorigenicity of cells in nude mice: Implication for implantation of metastases. Cancer Res. 46:3290–3294, 1986.

Pitot, H. C., L. E. Grosso, and T. Goldsworthy. Genetics and epigenetics of neoplasia: Facts and theories. In: Carcinogenesis. E. Huberman and S. H. Bart, editors. Raven Press, New York, 65–69, 1985.

Potter, K. M., S. J. Juacaba, J. E. Price, and D. Tarin. Observations on organ distribution of fluorescein-labelled tumour cells released intravascularly. Invasion Metastasis 3:221–233, 1983.

Ribi E., Clinical Immunology Newsletter 6:33, 1985.

Sampath, T. K., M. Muthukumaran, and A. H. Reddi. 1987. Isolation of osteogenin, and extracellular matrix-associated bone-inductive protein, by heparin affinity chromatography. Proc. Natl. Acad. Sci. U.S.A. 84:7109–7113, 1986.

Schuurmans, A. L. G., J. Bolt, and E. Mulder. Androgen receptor-mediated growth and epidermal growth factor receptor induction in human prostate cell line LNCaP. Urol. Int. 44:71–76, 1989.

Shearman, P. J., W. M. Gallatin, and B. M. Longenecker. Detection of a cell-surface antigen correlated with organ-specific metastasis. Nature 286:267–269, 1980.

Shevrin, D. H., S. L. Kukreja, L. Ghosh, and T. E. Lad. Development of skeletal metastasis by human prostate cancer in athymic nude mice. Clin. Expl. Metastasis 6:401–409, 1988.

Sonnenschein, C., N. Olea, M. E. Pasanen, and A. M. Soto. Negative controls of cell proliferation: Human prostate cancer cells and androgens. Cancer Res. 49:3474–3481, 1989.

Stamey, T. A., N. Yang, A. R. Hay, J. E. McNeal, F. S. Frieha, and E. Redwine. Prostate-specific antigen as a serum marker for adenocarcinoma of the prostate. New. Engl. J. Med. 317:909–916, 1987.

Story, M. T., J. Sasse, S. C. Jacobs, and R. K. Lawson. Prostatic growth factor: Purification and structural relationship to basic fibroblast growth factor. Biochemistry. 26:3843–3849, 1987.

Thompson, J. A., K. D. Anderson, J. M. DiPietro, J. A. Zwiebel, M. Zarnetta, W. FK. Anderson, and T. Maciag. Site-directed neovessel formation in vivo. Science 241:1349–1352, 1988.

Varani, J. Chemotaxis of metastatic tumor cells. Cancer Metastasis Rev. 1:17–28, 1982.

Wergedal, J. E., S. Mohan, A. K. Taylor, and D. J. Baylink. Skeletal growth factor is produced by human osteoblast-like cells in culture. Biochem. Biophys. Acta. 889:163–170, 1986.

Wilding, G., E. Valverius, C. Knabbe, and E. P. Gelmann. Role of transforming growth factor-alpha in human prostate cancer cell growth. The Prostate 15:1–12, 1989.

Zhang, H. Z., Ordonez, N. G., Batsakis, J. G., and Chan, J. C. Monoclonal antibody recognizing a carcinoembryonic antigen epitope differentially expressed in human colonic carcinoma versus normal adult colon tissues. Cancer Res. 49:5766–5773, 1989.

What is claimed is:

1. An isolated human prostate cell growth factor which stimulates prostate cell growth, the factor being obtained by a process that comprises the steps of:

(a) culturing human bone stromal cells in serum-conditioned media to produce conditioned media;

(b) passing said conditioned media over a heparin-affinity column in a low salt-containing buffer to bind the growth factor to the column;

(c) washing the column to remove one or more contaminants;

(d) eluting bound growth factor from the column with a high salt buffer;

(e) fractionating according to size; and (f) further purifying by subjecting said factor to non-reducing SDS-PAGE gel electrophoresis, and electroeluting the protein band having an apparent molecular weight of about 220 kD in said SDS-PAGE gel; and wherein said protein stimulates prostate cell growth.

2. The partially purified prostate cell growth factor according to claim 1 purified to between 10,000 to 100,000 units per milligram of protein.

3. The partially purified prostate cell growth factor according to claim 1 purified to between 100,000 to 500,000 units per milligram of protein.

4. The partially purified prostate cell growth factor according to claim 1 purified to between 500,000 to 900,000 units per milligram of protein.

5. An isolated human prostate cell growth factor comprising the following characteristics:

(a) the ability to stimulate the growth of LNCaP cells in soft agar in the presence of antibody against β-fibroblast growth factor, kerotinocyte growth factor, or hepatocyte growth factor;

(b) isolated from human bone stromal cell conditioned media and from human bone marrow aspirates;

(c) an molecular weight of about 220 kD when determined with a size-exclusion HPLC column; and (d) a biological activity that is heat sensitive and sensitive to trypsin.

6. The partially purified prostate cell growth factor according to claim 5 purified to between 10,000 to 100,000 units per milligram of protein.

7. The partially purified prostate cell growth factor according to claim 5 purified to between 100,000 to 500,000 units per milligram of protein.

8. The partially purified prostate cell growth factor according to claim 5 purified to between 500,000 to 900,000 units per milligram of protein.

9. A composition comprising an isolated human PSA stimulating autocrine factor (PSAF) including the following characteristics:

(a) the ability to stimulate androgen-independent prostate specific antigen (PSA) formation in human prostate cancer cells;

(b) isolated from human bone marrow aspirates;

(c) isolated from LNCaP sublines obtained from tumors maintained in castrated hosts;

(d) a biological activity that is heat sensitive and acid labile; and (e) a biological activity that is trypsin insensitive.

10. The composition of claim 9, further defined as a protein.

11. An isolated human PSA stimulating autocrine factor (PSAF) which stimulates androgen-independent prostate specific antigen (PSA) formation, the factor further being obtained by a process that comprises the steps of:

(a) obtaining LNCaP sublines from tumors maintained in castrated animal hosts;

(b) culturing the sublines in serum conditioned media to produce conditioned media;

(c) obtaining the growth factor by precipitation with about 60% to about 80% ammonium sulfate.

12. The factor according to claim 11 on a solid matrix.

13. The factor according to claim 12, wherein the matrix is foam or a sponge-like material.

14. The factor according to claim 12, wherein the matrix is agar or agarose.

15. A composition comprising a purified human growth factor polypeptide which stimulates anchorage-independent cell growth of prostate epithelial cells and includes the following characteristics:

(a) an approximate molecular weight of 157 kD as determined by SDS/PAGE in the absence or presence of β-mercaptoethanol or dithiothreitol when isolated from bone stromal cells;

(b) an approximate molecular weight of 157 kD as determined by non-reducing SDS/PAGE, and an approximate molecular weight of 55 kD as determined by reducing SDS/PAGE when isolated from bone marrow aspirates.

* * * * *

UNITED STATES PATENT AND TRADEMARK OFFICE
CERTIFICATE OF CORRECTION

PATENT NO.    :   5,728,815

DATED         :   March 17, 1998

INVENTOR(S)   :   Leland W.K. Chung, James Chan, Christopher Logothetis and Jer-Tsong Hsieh It is certified that error appears in the above-identified patent and that said Letters Patent is hereby corrected as shown below:

In claim 11, column 36, line 39, after 'produce conditioned media;', please insert -- and --.

Signed and Sealed this

Twenty-eighth Day of July, 1998

Attest:

BRUCE LEHMAN

*Attesting Officer*    *Commissioner of Patents and Trademarks*